(12) United States Patent
Chattopdhyay

(10) Patent No.: US 9,970,063 B2
(45) Date of Patent: May 15, 2018

(54) COMPOSITIONS AND METHODS FOR IDENTIFYING BACTERIAL CLONOTYPES AND DETECTING ANTIBIOTIC SUSCEPTIBILITY

(71) Applicant: ID Genomics, Inc., Seattle, WA (US)

(72) Inventor: Sujay Chattopdhyay, Seattle, WA (US)

(73) Assignee: ID Genomics, Inc., Seattle, WA (US)

( * ) Notice: Subject to any disclaimer, the term of this patent is extended or adjusted under 35 U.S.C. 154(b) by 0 days. days.

(21) Appl. No.: 15/055,376

(22) Filed: Feb. 26, 2016

(65) Prior Publication Data

US 2016/0251702 A1 Sep. 1, 2016

Related U.S. Application Data

(60) Provisional application No. 62/121,481, filed on Feb. 26, 2015, provisional application No. 62/279,643, filed on Jan. 15, 2016.

(51) Int. Cl.
*C12P 19/34* (2006.01)
*C12Q 1/68* (2018.01)

(52) U.S. Cl.
CPC ....... *C12Q 1/689* (2013.01); *C12Q 2600/106* (2013.01); *C12Q 2600/156* (2013.01); *C12Q 2600/158* (2013.01); *C12Q 2600/16* (2013.01)

(58) Field of Classification Search
USPC ............................. 435/6.12, 91.2
See application file for complete search history.

(56) References Cited

U.S. PATENT DOCUMENTS

2014/0193824 A1    7/2014  Sokurenko

FOREIGN PATENT DOCUMENTS

WO    2014/008312 A2    1/2014

OTHER PUBLICATIONS

Tchesnokova et al., J. Clin. Micro. 51(9), 2991-2999 (2013).*
Tchesnokova et al. "A Novel7-Single Nucleotide Polymorphism-Based Clonotyping Test 1-13 Allows Rapid Prediction of Antimicrobial Susceptibility of Extraintestinal *Escherichia coli* Directly From Urine Specimens." Open Forum Infect Dis. Jan. 18, 2016 (Jan. 18, 2016). vol. 3. pp. 1-7.
Tartof et al. Genotypic aanalyses of uropathogenic *E coil* based on fimH single nucleotide polymorphisms (SNPs). J. of Medical Microbiology 56:1363, 2007.
Johnson et al. Rapid and Specific Detection, Molecular Epidemiology, and Experimental Virulence of the O16 Subgroup within *E coli* Sequence Type 131. J. of Clinical Microbiology 52:1358, 2014.
Dias et al. Use of fimH Single Nucleotide Polymorphisms for Strain Typing of Clinical Isolates of *E coli* for Epidemiologic Investigation. J. of Clinical Microbiology 48:483, 2010.
Stahlhut et al., Population Variability of the FimH Type 1 Fimbrial Adhesin in *Klebsiella pneumoniae* J. of Bacteriology, 191: 1941, 2009.

* cited by examiner

*Primary Examiner* — Kenneth Horlick
(74) *Attorney, Agent, or Firm* — Seed IP Law Group LLP

(57) ABSTRACT

There is disclosed a PCR-based test kit and PCR process for identification of multiple clonal sub-species lineages of infectious bacteria, such as uropathogenic *E. coli* causing cystitis. pyelonephritis and urosepsis, for the purposes of predicting antibiotic resistance of the bacteria. More specifically, there is further disclosed a SNP (single nucleotide polymorphism) identification process that simultaneously detect compilations of the presence of absence of predictive SNPs within mutated loci of infectious bacterial clonal subspecies variants, such as the fumC/fimH loci of the *E. coli* bacterium. This disclosure provides a PCR detection kit incorporating a SNP compilation that forms a BFC (Binary Footprint Code) that allows for rapid identification of multiple infectious bacterial clonotypes based on their SNP footprint. More specifically there is disclosed a clonotyping method for clonal typing *E. coli* and predicting antibiotic susceptibility, comprising (a) providing forward primers and reverse primers for at least seven SNPs (single nucleotide polymorphisms) selected from the group consisting of fumC-63, fumC-248, fumC-380, fimH-162, fimH-233, fimH-483, and fimH-108, (b) measuring the presence or absence of each SNP, and (c) determining antibiotic susceptibility from Lookup Table 1.

20 Claims, 18 Drawing Sheets
(10 of 18 Drawing Sheet(s) Filed in Color)

Lookup Table 1. Lookup table for cumulative antibiotic susceptibility of individual 7-types.

| 7-type number | fumC-63 | fumC-248 | fumC-380 | fimH-108 | fimH-162 | fimH-233 | fimH-483 | A/C | CZ | CTR | T/S | CIP | NIT | Don't use antibiotic/s |
|---|---|---|---|---|---|---|---|---|---|---|---|---|---|---|
| 200 | - | + | - | - | - | - | - | 100 | 100 | 100 | 100 | 100 | 100 | - |
| 220 | - | + | - | - | + | - | - | 100 | 100 | 100 | 100 | 100 | 100 | - |
| 221 | - | + | - | - | + | - | + | 100 | 73 | 77 | 100 | 100 | 100 | AMP,A/C,T/S |
| 230 | - | + | - | - | + | + | - | 100 | 81 | 78 | 86 | 78 | 77 | AMP,A/C,CZ,T/S,CIP |
| 231 | - | + | - | + | + | + | + | 100 | 100 | 100 | 97 | 97 | 97 | AMP,CZ,NIT |
| 251 | - | + | - | + | + | + | + | 100 | 100 | 100 | 75 | 100 | 75 | AMP,A/C,CZ,CTR,T/S,CIP |
| 261 | - | + | - | + | + | + | + | 100 | 75 | 76 | 71 | 100 | 71 | AMP,A/C,CZ,CTR,T/S,CIP,ESBL |
| 271 | - | + | - | - | + | - | + | 100 | 73 | 80 | 81 | 86 | 85 | AMP,A/C,CZ,T/S |
| 320 | - | + | - | - | + | - | - | 100 | 100 | 100 | 99 | 100 | 97 | AMP,A/C |
| 330 | - | + | - | + | + | + | - | 100 | 100 | 100 | 100 | 100 | 100 | - |
| 331 | - | + | + | - | + | - | + | 100 | 76 | 81 | 100 | 86 | 100 | AMP,A/C |
| 341 | - | + | + | + | - | + | - | 100 | 100 | 100 | 100 | 100 | 100 | NIT |
| 351 | - | + | + | + | - | + | + | 72 | 88 | 75 | 100 | 100 | 100 | AMP,A/C,CZ,NIT |
| 360 | - | + | + | + | + | + | + | 100 | 100 | 84 | 100 | 100 | 100 | AMP |
| 371 | - | + | + | + | + | + | + | 100 | 100 | 75 | 100 | 92 | 75 | AMP,CZ,T/S,CIP,ESBL |
| 421 | + | - | + | - | + | - | - | 100 | 100 | 100 | 100 | 100 | 100 | - |
| 430 | + | - | + | - | + | + | - | 100 | 100 | 100 | 100 | 100 | 100 | - |
| 461 | + | - | + | - | + | - | + | 100 | 100 | 77 | 97 | 87 | 89 | AMP,A/C,CZ |
| 471 | + | - | + | + | + | + | - | 100 | 78 | 100 | 100 | 73 | 100 | AMP,A/C,CZ,T/S |
| 500 | + | - | - | - | + | - | - | 100 | 100 | 100 | 100 | 75 | 100 | T/S |
| 520 | + | - | - | - | + | + | - | 100 | 78 | 83 | 84 | 100 | 100 | AMP,A/C,T/S |
| 521 | + | - | + | - | + | - | + | 100 | 100 | 75 | 90 | 100 | 100 | AMP,A/C,CZ,CTR,T/S,ESBL |
| 530 | + | - | + | - | + | + | - | 100 | 100 | 100 | 100 | 100 | 100 | - |
| 531 | + | - | + | - | + | + | + | 100 | 100 | 73 | 76 | 78 | 97 | AMP,A/C,CZ,CTR,T/S,CIP,ESBL |
| 540 | + | - | + | + | + | - | - | 100 | 100 | 100 | 96 | 100 | 96 | AMP,A/C,CZ,T/S |

| 7-type TRIPLET number | fumC-63 | fumC-248 | fumC-380 | fimH-108 | fimH-162 | fimH-233 | fimH-483 | A/C | CZ | CTR | T/S | CIP | NIT | Don't use antibiotic/s |
|---|---|---|---|---|---|---|---|---|---|---|---|---|---|---|
| 751 | + | + | + | + | - | + | + | | | 76 | 88 | | | AMP,A/C,CZ,T/S,CIP |
| 760 | + | + | + | + | + | - | - | 100 | 100 | 100 | 100 | 100 | 100 | - |
| 761 | + | + | + | + | + | - | + | 73 | 88 | 95 | 100 | 98 | 98 | AMP |
| 771 | + | + | + | + | + | + | + | | 78 | 89 | 93 | 72 | 87 | AMP,A/C,T/S |

Fig. 8C

*fumC* (allele 4) 469 bp fragment 40

5'- CGAGGGCCATTGGAGCAGGCGGCGGAGTGAAGTACTGGCAGGACAGCATGACGACGAATTCCCGTGGCTAT
CTGGCAGACCGGCTCCGGCACGCAAAGTAACATGAACGAAGTGCTAACCGGCCAGTGAATTA
CTCGGCGGCGTGCGGATGGAACGTAAAGTTCACCCTAACGACGACGTGAACAAAAGCAAAGTTCCAAC
GATGTCTTTCCGACGGCGATGCACGTTGCGGCCTCTGGCGGCTGCGCAAGCAACTCATTCCGCAGCTTA
AAACCCTGACACAGACACTGAGTGAAAAATCGGTGCATTGCCGATATCGTCAAAATCGGTCGAACCACTG
CAGGACGCCACCGCCGCTAACGCTAGGGCAGGAGATTTCCGGCTGGGTAGGCGATGCTCGAGCATAATCTC
AAACATATCGAATACAGCCTGCCCTCACGTAGCGGAACTGGCTCTCGGGCGTACAGCGGTGGGTACTGACTA
AATACCCATCCGGAATATGCGGGCGTCGCTAGCAGATGAACTGGCAGTCATTACCGTGCACCGTTGTACCGCG
CCGAACAAATTGAAGGCGTCGACCTGTGATGCCCTCGTCAGGCGCACGGCCATGAAGGGTTGGCTGCG
TCACTGATGAAATGCCAATGATGCCTCGCCTCTGGCCGCGTGCCGAATTGGTGAAATCTCAATCC
GGAAATGAGCCGGCAGTCAATCATGCCAGGAAAGTGAACCAACAGTGCGAAGCATTAACCATGCTCT
GCTGTCAGTGATGGGGAACGCAGTGGATCAACAGCGTGGCGCTTCCGGTAACTTTGAACTGAACGTCTTCC
GTCCGATGGTGATCCATAATTTCCGCAATCGGTCGCTTGCTGCAGATGGCATGGAAAGTTCAACAAACACT
GTGCAGTGCCGGCATTGAACCGAATCG -3' (SEQ ID NO. 3)

*Fig. 9*

*fimH* (allele 27) 489 bp fragment30

5'- TTCGCCTGTAAAACCGCCAATGGTACCGCTATCCCTATTGGCGGTGGCAGGCCAATGTTTATGTAAACCTTGCG
CCGTCGTCAGAATGTGGGGCAAAACCTGGCTGTGATCTTTCGACGCAAATCTTTGCCATAACGATTATC
CGGAAACCATTACAGATATGTCACACTGCAAGAGGCTCGGCTTATGGCGGCGTGTATCTAATTTTTCC
GGGACCGTAAAATATATCTGGCAGTAGCTATCCATTTCCTACCACCAGGAAAGCGCCGGTGTTTAT
AATTCGAGAACGGATAAGCCGTGGCCGGGTGGCCGGCTTTATTTGACGCCTGTGAGCAGTGCGGGCGGGGTGGCG
ATTAAAGTGGCTCATAATTGCCGTGCTTATTTGCGACAGACCAACAACTATAACGACGATGATTCCAGTTT
GTGTGGAATATTTACGCCAATAATGATGTGGTGCTACTGGCCGGGCTGGATGCTTCTGCTCGTGATG
TCACCGTTACTCTGCCGGACTACCCTGGTTCAGTGCCGATTCCCTTACCGTTATTGTGCGAAAAGCCAAACC
TGGGGTATTACCTATCCGGCACAACCGGCAGATGCGGGCAACTGGATTTTCACCAATACCGGTCGTTTCACCC
GCGCAGGGGGGTCGGGTTACAGTTGACGCGCAACGGTACGCCAACGATTATTCCAGCGAATAACACGGTATCGTTAGGAGC
AGTAGGGACTTCGGCGGTAAGTCTGGGATTAACGGCAAATTACGCACGTACCGGAGGGCAGGTGACTGCAGGG
AATGTGCAATCGATTATTGGCGGTGACTTTTGTTTATCAATAA - 3' (SEQ ID NO. 4)

*Fig. 10*

Table 10: Antibiotic profiles of major septatypes from the reference *E. coli* collection (Lookup Table)

| Septatype | % isolates | Ampicillin | Amoxi-Clav | Cefazolin | Ceftriaxone | Trim-Sulfa | Ciprofloxacin | Nitrofurantoin |
|---|---|---|---|---|---|---|---|---|
| All | 100 | 45 | 15 | 16 | 3.7 | 21 | 14 | 1.3 |
| 620 | 9.8 | 48 | 23 | 20 | 0.8 | 15 | 4.2 | 0.8 |
| 530 | 9.2 | 27 | 7.1 | 5.3 | 0 | 5.3 | 0.9 | 0 |
| 271 | 7.9 | 75 | 19 | 20 | 5.2 | 56 | 14 | 0 |
| 760 | 7.7 | 23 | 4.2 | 4.2 | 0 | 6.3 | 4.2 | 3.2 |
| 561 | 7.4 | 75 | 31 | 38 | 13 | 45 | 86 | 4.4 |
| 361 | 4.9 | 38 | 12 | 13 | 6.7 | 17 | 8.3 | 1.7 |
| 571 | 4.2 | 73 | 12 | 9.8 | 0 | 24 | 25 | 2 |
| 371 | 3.7 | 57 | 33 | 22 | 13 | 43 | 30 | 6.5 |
| 721 | 3.7 | 22 | 4.4 | 6.7 | 0 | 6.7 | 2.2 | 0 |
| 360 | 3.3 | 48 | 13 | 15 | 2.5 | 18 | 15 | 0 |
| 771 | 3.1 | 47 | 13 | 13 | 5.3 | 39 | 11 | 2.6 |
| 531 | 3 | 16 | 0 | 27 | 0 | 0 | 0 | 0 |
| 731 | 2.9 | 25 | 0 | 2.8 | 0 | 2.8 | 2.8 | 2.8 |
| 131 | 2.6 | 53 | 47 | 44 | 3.1 | 31 | 3.1 | 0 |
| 511 | 2.6 | 31 | 16 | 13 | 3.1 | 63 | 0 | 0 |
| 661 | 2.5 | 32 | 19 | 16 | 0 | 3.2 | 0 | 0 |
| 510 | 2.1 | 50 | 31 | 38 | 3.8 | 15 | 0 | 0 |
| 560 | 2.1 | 77 | 12 | 3.8 | 3.8 | 38 | 12 | 0 |
| 351 | 1.9 | 39 | 13 | 13 | 8.7 | 26 | 17 | 0 |
| 761 | 1.9 | 39 | 17 | 43 | 0 | 22 | 43 | 0 |
| 261 | 1.4 | 41 | 0 | 12 | 0 | 18 | 0 | 5.9 |
| 520 | 1.4 | 38 | 13 | 13 | 6.3 | 19 | 0 | 0 |
| 751 | 1.4 | 29 | 18 | 18 | 12 | 29 | 29 | 0 |
| 260 | 1.1 | 50 | 14 | 7.1 | 7.1 | 21 | 14 | 0 |
| 231 | 1 | 75 | 25 | 25 | 8.3 | 58 | 17 | 0 |
| 630 | 1 | 17 | 8.3 | 17 | 0 | 0 | 0 | 0 |

*Fig. 11*

Table 11: Reference Lookup-Table resistance

| | Ampicillin | Amoxi-Clav | Cefazolin | Ceftriaxone | Trim-Sulfa | Ciprofloxacin | Nitrofurantoin | ESBL |
|---|---|---|---|---|---|---|---|---|
| Reference set isolates | 44.7 | 18.4 | 15.5 | 3.7 | 21.4 | 13.7 | 1.3 | 2.0 |
| Field trial isolates | 55.6 | 21.2 | 12.2 | 4.8 | 25.8 | 21.5 | 2.9 | 4.5 |

*Fig. 12*

Table 12

| Class of prescribed antibiotics | Resistance rate in GH UC E. coli | Prescription rate (out of 236 cases) |
|---|---|---|
| Ampicillin or amoxicillin | 55.3% | 1.3% |
| Amoxi-Clav | 25.6% | 0.8% |
| Trim-Sulfa | 25.7% | 28.4% |
| Cipro or Levo | 21.5% | 51.7% |
| Cefazolin etc. | 12.8% | 8.1% |
| Nitrofurantoin | 2.9% | 5.5% |
| Cefuroxime or ceftriaxone etc. | 5.4% | 3.0% |

*Fig. 13*

Table 13

| Class of prescribed antibiotics | Resistance rate in GH UC E. coli | Prescription rate (out of 236 cases) | Drug-bug mismatch (41 cases) |
|---|---|---|---|
| Ampicillin or amoxicillin | 55.8% | 1.3% | 33% |
| Amoxi-Clav | 25.6% | 0.8% | 50% |
| Trim-Sulfa | 25.7% | 28.4% | 20.9% |
| Cipro or Levo | 21.5% | 51.7% | 15.6% |
| Cefazolin etc. | 12.8% | 8.1% | 10.5% |
| Nitrofurantoin | 2.9% | 5.5% | 0.0% |
| Cefuroxime or ceftriaxone etc. | 5.4% | 3.0% | 14.3% |
| TOTAL | | | 17.4% |

*Fig. 14*

Table 14

| Class of prescribed antibiotics | Resistance rate in GH UC E. coli | Prescription rate (out of 236 cases) | Drug-bug mismatch | Prescription allowed by CLT Test |
|---|---|---|---|---|
| Ampicillin or amoxicillin | 55.8% | 1.3% | 33% | 1.7% |
| Amoxi-Clav | 25.6% | 0.8% | 50% | 54.0% |
| Trim-Sulfa | 25.7% | 28.4% | 20.9% | 34.7% |
| Cipro or Levo | 21.5% | 51.7% | 15.6% | 75.6% |
| Cefazolin etc. | 12.8% | 8.1% | 10.5% | 56.4% |
| Nitrofurantoin | 2.9% | 5.5% | 0.0% | 100% |
| Cefuroxime or ceftriaxone etc. | 5.4% | 3.0% | 14.3% | 100% |
| TOTAL | | | 17.4% | |

*Fig. 15*

Table 15

| Class of prescribed antibiotics | Resistance rate in GH UC E. coli | Prescription rate (out of 236 cases) | Drug-bug mismatch | Prescription allowed by CLT Test | Drug-Bug mismatch after CLT Test |
|---|---|---|---|---|---|
| Ampicillin or amoxicillin | 55.8% | 1.3% | 33% | 1.7% | 0.0% |
| Amoxi-Clav | 25.6% | 0.8% | 50% | 34.0% | 5.1% |
| Trim-Sulfa | 25.7% | 28.4% | 20.9% | 34.7% | 5.9% |
| Cipra or Levo | 21.5% | 51.7% | 15.6% | 75.6% | 5.9% |
| Cefazolin etc. | 12.8% | 8.1% | 10.5% | 56.4% | 3.7% |
| Nitrofurantoin | 2.9% | 5.5% | 0.0% | 100% | 2.0% |
| Cefuroxime or ceftriaxone etc. | 5.4% | 3.0% | 14.3% | 100% | 4.8% |
| TOTAL | | | 17.4% | | 4.3% |

*Fig. 16*

SEQUENCE LISTING

```
<160> NUMBER OF SEQ ID NOS: 22

<210> SEQ ID NO 1
<211> LENGTH: 22
<212> TYPE: DNA
<213> ORGANISM: Escherichia coli

<400> SEQUENCE: 1
cactcaggga accattcagg ca                                             22

<210> SEQ ID NO 2
<211> LENGTH: 21
<212> TYPE: DNA
<213> ORGANISM: Escherichia coli

<400> SEQUENCE: 2
cttattgata aacaaagtca c                                              21

<210> SEQ ID NO 3
<211> LENGTH: 970
<212> TYPE: DNA
<213> ORGANISM: Escherichia coli

<400> SEQUENCE: 3
cgagcgccat tcggcaggcg gcggatgaag tactggcagg acagcatgac gacgaattcc    60
cgctggctat ctggcagacc ggctccggca cgcaaagtaa catgaacatg aacgaagtgc   120
tggctaaccg ggccagtgaa ttactcggcg gcgtgcgcgg gatggaacgt aaagttcacc   180
ctaacgacga cgtgaacaaa agccaaagtt ccaacgatgt ctttccgacg gcgatgcacg   240
ttgcggcgct gctggcgctg cgcaagcaac tcattccgca gcttaaaacc ctgacacaga   300
cactgagtga aaaatcgcgt gcatttgccg atatcgtcaa aatcggtcga acccacttgc   360
aggacgccac gccgctaaca ctagggcagg agatttccgg ctgggtagcg atgctcgagc   420
ataatctcaa acatatcgaa tacagcctgc ctcacgtagc ggaactggct ctgggcggta   480
cagcggtggg tactggacta aatacccatc cggaatatgc gcgtcgcgta gcagatgaac   540
tggcagtcat tacctgtgca ccgtttgtta ccgcgccgaa caaatttgaa gcgctggcga   600
cctgtgatgc cctggtcagg cgcacggcgc attgaaaggg ttggctgcgt cactgatgaa   660
aattgccaat gatgtccgct ggctgctctg gcccgcgctg cggaattggt gaaatctcaa   720
tcccggaaaa tgagccgggc agctcaatca tgccaggaaa gtgaacccaa cacagtgcga   780
agcattaacc atgctctgct gtcaggtgat ggggaacgac gtgggatcaa catgggtggc   840
```

```
gcttccggta actttgaact gaacgtcttc cgtccgatgg tgatccataa tttccgcaat    900
cggtgcgctt gctggcagat ggcatggaaa gtttcaacaa acactgtgca gtgggcattg    960
aaccgaatcg                                                           970
```

<210> SEQ ID NO 4
<211> LENGTH: 840
<212> TYPE: DNA
<213> ORGANISM: Escherichia coli

<400> SEQUENCE: 4

```
ttcgcctgta aaaccgccaa tggtaccgct atccctattg gcggtggcag cgccaatgtt     60
tatgtaaacc ttgcgcccgt cgtgaatgtg gggcaaaacc tggtcgtgga tctttcgacg    120
caaatctttt gccataacga ttatccggaa accattacag actatgtcac actgcaacga    180
ggctcggctt atggcggcgt gttatctaat ttttccggga ccgtaaaata tagtggcagt    240
agctatccat ttcctaccac cagcgaaacg ccgcgcgttg tttataattc gagaacggat    300
aagccgtggc cggtggcgct ttatttgacg cctgtgagca gtgcgggcgg ggtggcgatt    360
aaagctggct cattaattgc cgtgcttatt ttgcgacaga ccaacaacta taacagcgat    420
gatttccagt ttgtgtggaa tatttacgcc aataatgatg tggtggtgcc tactggcggc    480
tgcgatgctt ctgctcgtga tgtcaccgtt actctgccgg actacctgg ttcagtgccg     540 attcctctta ccgtttattg tgcgaaaagc caaaacctgg ggtattacct atccggcaca    600
accgcagatg cgggcaactc gattttcacc aataccgcgt cgttttcacc cgcgcagggc    660
gtcggcgtac agttgacgcg caacggtacg attattccag cgaataacac ggtatcgtta    720
ggagcagtag ggacttcggc ggtaagtctg ggattaacgg caaattacgc acgtaccgga    780
gggcaggtga ctgcagggaa tgtgcaatcg attattggcg tgacttttgt ttatcaataa    840
```

<210> SEQ ID NO 5
<211> LENGTH: 21
<212> TYPE: DNA
<213> ORGANISM: Escherichia coli

<400> SEQUENCE: 5

```
agcatgacga cgaattcctg c                                              21
```

<210> SEQ ID NO 6
<211> LENGTH: 21
<212> TYPE: DNA
<213> ORGANISM: Escherichia coli

<400> SEQUENCE: 6

```
gtcgtcgtta gggtgaactt t                                              21
```

<210> SEQ ID NO 7
<211> LENGTH: 21
<212> TYPE: DNA
<213> ORGANISM: Escherichia coli

<400> SEQUENCE: 7

```
acggcgatgc acgttgcgtc g                                              21
```

<210> SEQ ID NO 8
<211> LENGTH: 21
<212> TYPE: DNA
<213> ORGANISM: Escherichia coli -continued

```
<400> SEQUENCE: 8
agttccgcta cgtgaggcag g                                          21

<210> SEQ ID NO 9
<211> LENGTH: 21
<212> TYPE: DNA
<213> ORGANISM: Escherichia coli

<400> SEQUENCE: 9
agttccgcta cgtgaggcag g                                          21

<210> SEQ ID NO 10
<211> LENGTH: 21
<212> TYPE: DNA
<213> ORGANISM: Escherichia coli

<400> SEQUENCE: 10
agttccgcta cgtgaggcag g                                          21

<210> SEQ ID NO 11
<211> LENGTH: 21
<212> TYPE: DNA
<213> ORGANISM: Escherichia coli

<400> SEQUENCE: 11
caggacgcga cgccgctcac g                                          21

<210> SEQ ID NO 12
<211> LENGTH: 21
<212> TYPE: DNA
<213> ORGANISM: Escherichia coli

<400> SEQUENCE: 12
caggatgcga cgccgctcac g                                          21

<210> SEQ ID NO 13
<211> LENGTH: 21
<212> TYPE: DNA
<213> ORGANISM: Escherichia coli

<400> SEQUENCE: 13
gtggagcaaa acctggtctt g                                          21

<210> SEQ ID NO 14
<211> LENGTH: 21
<212> TYPE: DNA
<213> ORGANISM: Escherichia coli

<400> SEQUENCE: 14
agggaaagga tagctactgc c                                          21

<210> SEQ ID NO 15
<211> LENGTH: 21
<212> TYPE: DNA
<213> ORGANISM: Escherichia coli

<400> SEQUENCE: 15
tatccggaaa ccattacaga c                                          21

<210> SEQ ID NO 16
<211> LENGTH: 21
<212> TYPE: DNA
<213> ORGANISM: Escherichia coli
```

```
<400> SEQUENCE: 16
tcaaataaag cgccaccggc c                                              21

<210> SEQ ID NO 17
<211> LENGTH: 21
<212> TYPE: DNA
<213> ORGANISM: Escherichia coli

<400> SEQUENCE: 17
ttccgagacc gtaaaatata g                                              21

<210> SEQ ID NO 18
<211> LENGTH: 21
<212> TYPE: DNA
<213> ORGANISM: Escherichia coli

<400> SEQUENCE: 18
tcaaataaag cgccaccggc c                                              21

<210> SEQ ID NO 19
<211> LENGTH: 21
<212> TYPE: DNA
<213> ORGANISM: Escherichia coli

<400> SEQUENCE: 19
gtggtggcta ctggcggcag c                                              21

<210> SEQ ID NO 20
<211> LENGTH: 21
<212> TYPE: DNA
<213> ORGANISM: Escherichia coli

<400> SEQUENCE: 20
gtggtggcta ctggcggcag c                                              21

<210> SEQ ID NO 21
<211> LENGTH: 20
<212> TYPE: DNA
<213> ORGANISM: Escherichia coli

<400> SEQUENCE: 21
tcttgccgtt ttcgtcggta                                                20

<210> SEQ ID NO 22
<211> LENGTH: 0
<212> TYPE: DNA
<213> ORGANISM: Escherichia coli

<400> SEQUENCE: 22

000
```

COMPOSITIONS AND METHODS FOR IDENTIFYING BACTERIAL CLONOTYPES AND DETECTING ANTIBIOTIC SUSCEPTIBILITY

CROSS REFERENCE TO RELATED APPLICATION

This patent application claims priority from U.S. provisional patent application 62/121,481 filed 26 Feb. 2015, and U.S. provisional patent application 62/279,643 Filed 15 Jan. 2016.

The present patent application was made, in part, with the support of NIH grant RO1AI106007 to the University of Washington, and NIH grant R41AI116114 to ID Genomics, Inc. The federal government has certain rights to this invention.

TECHNICAL FIELD

The present disclosure provides a PCR-based test kit and nucleic acid amplification process for identification of multiple clonal sub-species lineages of infectious bacteria, such as uropathogenic *E. coli* causing cystitis, pyelonephritis and urosepsis, for the purposes of predicting antibiotic resistance of the bacteria. More specifically, the present disclosure provides a SNP (single nucleotide polymorphism) identification process that simultaneously detects compilations of the presence of absence of predictive SNPs within mutated loci of infectious bacterial clonal subspecies variants, such as the fumC/fimH loci of *E. coli* bacterium. The disclosure provides a nucleic acid amplification detection kit incorporating a SNP compilation that forms a BFC (Binary Footprint Code) that allows for rapid identification of multiple infectious bacterial clonotypes based on their SNP footprint. More specifically the present disclosure provides a clonotyping method for clonal typing *E. coli* and predicting antibiotic susceptibility, comprising (a) providing forward primers and reverse primers for at least seven SNPs (single nucleotide polymorphisms) selected from the group consisting of fumC-63, fumC-248, fumC-380, fimH-162, fimH-233, fimH-483, and fimH-108, (b) measuring the presence or absence of each SNP, and (c) determining antibiotic susceptibility from Lookup Table 1. The disclosed clonotyping test and kits provided herewith can rapidly identify clonal types of *E. coli* directly from urine specimens, demonstrating the ability to better predict antibiotic resistance using a clonal diagnostics approach in a point-of-care setting.

BACKGROUND

The increasing prevalence of antimicrobial-resistant pathogens is one of the greatest challenges in clinical medicine today. Current culture-based approaches typically require 2-3 days to produce a susceptibility profile. Thus, the choice of empirical antimicrobial therapy is based on the most likely causative species and the species' most recent cumulative antibiogram for the region or hospital. Unfortunately, the empirical treatment now leads to potential 'drug-bug' mismatches in up to 25% of prescriptions and it is estimated that up to 50% of antibiotics are used inappropriately (Antibiotic Resistance Threats in the United States of America. CDC Report 2013; and Tchesnokova et al., J. Clin. Microbiol. 2013 September; 51(9):2991-2999.). Rapid molecular tools have been explored as a way to refine this process by targeting the genetic markers of resistance (Kalashnikov et al., *Lab Chip* 2012; Romero-Gomez *J. Infect.* 2012; Koser et al., *PLoS Pathog.* 2012; 8:e1002824; and Schofield et al., *J. Microbiol. Methods* 2012; 90:80-82). However, resistance to the same drug within same species very often depends on presence (and proper expression) of a wide range of specific genes or mutant variants (Arias et al., *N. Engl. J. Med.* 2009; 360:439-443; and Chenia et al., *J. Antimicrob. Chemother.* 2006; 58:1274-1278). Thus, it still remains unfeasible to predict resistance and, especially, susceptibility to multiple clinically relevant antibiotics by a single test that is based on the gene markers approach. Therefore, there is an urgent need to introduce novel tests and approaches to improve near-patient empirical treatment decisions to lower the risks associated with inappropriate antimicrobial use.

The increasing prevalence of antimicrobial-resistant pathogens is one of the greatest challenges in clinical medicine today (Alanis, *Arch. Med. Res.* 36:697-705, 2005; and Spellberg et al., *Clin. Infect. Dis.* 46:155-164, 2008.). Since current culture-based approaches typically require 1.5-3 days to produce a susceptibility profile, the patient's treatment usually must begin before the provider knows whether the antibiotic is likely to work or the treatment will be optimal with respect to cost, duration, and/or antimicrobial spectrum. The choice of empirical antimicrobial therapy must be based on the type of infection, the most likely causative species, and the species' typical susceptibility profiles (Jenkins and Schuetz. *Mayo Clin. Proc.* 87:290-308, 2012; and Dellit et al., *Clin. Infect. Dis.* 44:159-177, 2007). However, preferred antibiotics now encounter potential 'drug-bug' mismatches in up to 25% of prescriptions (Tchesnokova et al., *J. Clin. Microbiol.* 51(9):2991-2999, September 2013) and it is estimated that up to 50% of antibiotics are used inappropriately. Thus, there is an urgent need to provide physicians with rapid antimicrobial assays that guide appropriate treatment decisions to minimize risks associated with inappropriate or ineffective antimicrobial use.

Urinary tract infections are the most common bacterial infections in women and are caused primarily by *E. coli*. *E. coli* is a leading bacterial pathogen that, in developed countries, causes mainly UTI and bloodstream infections, resulting in millions of infections and tens of thousands of deaths each year in the United States alone. Like most bacterial pathogens, *E. coli* is a clonal species, with the pathogenic strains belonging to a limited number of genetically related lineages (i.e., clonotypes). Although certain *E. coli* clonotypes are known to have distinctive antimicrobial susceptibility patterns, the use of clonotyping as a general predictive marker for antimicrobial susceptibility has not been introduced into clinical practice. The main reason for this is that the most-commonly used clonal typing methods, multilocus sequence typing (MLST) and pulsed-field gel electrophoresis (PFGE), are not suited for diagnostics purposes due to their high costs, slow turnaround, and low prognostic values.

Urinary tract infections are the most common bacterial infections in women and elders that are caused primarily by *E. coli* and, in USA, results in millions of infections and tens of thousands of deaths (mostly from urosepsis) each year (Foxman, *Nat. Rev. Urol.* 2010 Dec.; 7(12):653-60; and Russo and Johnson, 2003 *Microbes Infect.* 5:449-456.). Like most bacterial pathogens, *E. coli* is a clonal species, with the pathogenic strains belonging to a limited number of genetically related lineages (i.e., clonotypes) that have distinctive antimicrobial susceptibility patterns (Wright et al., 2013. *Am. J. Infect. Control* 41:33-38; Peterson et al., 2012. *Infect Control Hosp. Epidemiol.* 33:790-795; Wright et al., *Infect. Control Hosp. Epidemiol.* 32:635-640, 2011; Johnson et al., J. Infect. Dis. 207:919-928, 2013; Am. J. Infect. Control 38:350-353, 2010; and La Forgia Am. J. Infect. Control 38:259-263, 2010). However, the most-commonly used clonal typing methods, multilocus sequence typing (MLST) and pulsed-field gel electrophoresis (PFGE) are not suited for diagnostics purposes due to their high costs, slow turn-around, and low prognostic values.

Others have tried, without much success, to develop rapid molecular tools as a way to refine this process (Kalashnikov et al. Lab Chip 2012; Romero-Gomez et al., J. Infect. 2012; Koser et al., PLoS Pathog. 2012; 8:e1002824; and Schofield et al. J. Microbiol. Methods 90:80-82, 2012), but since a wide range of genes and point mutations can confer resistance to the same drug, even within same species (Arias and Murray, N. Engl. J. Med. 360:439-443, 2009; and Chenia et al. J. Antimicrob. Chemother. 2006; 58:1274-8, 2006), detection of the broad scope of resistance determinants in one test remains unfeasible for routine clinical diagnostics.

In any medical treatment center, such as a hospital emergency care facility, patients presenting with bacterial infections need urgent treatment so as to prevent and treat any infection before the patient becomes septic. However, the choice of treatment with an antibiotic will depend on whether the infecting bacterial organism is resistant or susceptible to a particular antibiotic. The answer to that question has historically been done by culturing the infecting organism on an agar plate and adding antibiotic-soaked paper to the surface of the agar. The information which antibiotic is resistant or not can be achieved in a few days. But the treating physician does not have a few days to wait to find the correct answer. Instead, the treating physician has to guess which antibiotic(s) will work and balance the likelihood of resistance with side effect profiles of each antibiotic. Therefore, there is a significant need in the art for a process and test kit that can rapidly (i.e., within an hour) provide a better prediction of treatment choice based on the specific clonal subspecies of bacteria causing a patient's infection. The present disclosure provides a test kit and process to address that need.

Multilocus sequence typing (MLST) is often based on sequencing 5-8 housekeeping loci in a bacterial chromosome to provide descriptions of the bacterial species present. However, even strains with identical MLST profiles (known as sequence types or STs) may possess distinct genotypes, which enable different eco- or pathotypic lifestyles. Multilocus sequence typing (MLST) is a method for characterizing relatedness of strains within bacterial species (Maiden et al., Proc. Natl. Acad. Sci. USA 95:3140-3145, 1998). Standardized MLST schemes have been established for human pathogens, including E. coli (Wirth et al., Mol. Microbiol. 60:1136-1151, 2006). Certain E. coli sequence types are epidemiologically associated with specific extra-intestinal syndromes, such as ST127 and ST73 with pyelonephritis (Johnson et al., J. Clin. Microbiol. 46:417-422, 2008; and Johnson et al. Microbes Infect. 8:1702-1713, 2006). Others have shown emerging antimicrobial resistance properties, such as ST69 with trimethoprim/sulfamethoxazole resistance (Manges et al., N. Engl. J. Med. 345:1007-1013, 2001) and ST131 with fluoroquinolone resistance and extended-spectrum beta-lactamase production (Nicolas-Chanione et al., J. Antimicrob. Chemother. 61, 273-281, 2008).

BRIEF SUMMARY

The present disclosure provides a PCR-based test kit and PCR process for identification of multiple clonal sub-species lineages of infectious bacteria, such as uropathogenic E. coli causing cystitis, pyelonephritis and urosepsis, for the purposes of predicting antibiotic resistance of the bacteria. More specifically, the present disclosure provides a SNP (single nucleotide polymorphism) identification process that simultaneously detects the presence of absence of predictive SNPs within mutated loci of infectious bacterial clonal subspecies variants, such as the fumC/fimH loci of the E. coli bacterium. This disclosure provides a PCR detection kit incorporating a seven SNP compilation that forms a BFC (Binary Footprint Code) that allows for rapid identification of multiple infectious bacterial clonotypes based on their SNP footprint.

The present disclosure provides a clonotyping (specifically called 7t, CLT or SNP-7 herein) method for clonal typing E. coli and predicting antibiotic susceptibility, comprising (a) providing forward primers and reverse primers for at least seven SNPs (single nucleotide polymorphisms) selected from the group consisting of fumC-63, fumC-248, fumC-380, fimH-162, fimH-233, fimH-483, and fimH-108, and (b) a Lookup Table. Preferably, the Lookup Table is Lookup Table 1.

The present disclosure provides a kit for clonotyping E. coli and predicting antibiotic susceptibility, comprising (a) forward primers and reverse primers for at least seven SNPs (single nucleotide polymorphisms) selected from the group consisting of fumC-63, fumC-248, fumC-380, fimH-162, fimH-233, fimH-483, and fimH-108, and (b) a Lookup Table. Preferably, the Lookup Table is Lookup Table 1.

The present disclosure provides a PCR-based test kit and PCR process for identification of multiple clonal sub-species lineages of uropathogenic E. coli causing cystitis, polynephritis and urosepsis for the purposes of predicting antibiotic resistance of the bacteria. More specifically, the present disclosure provides a SNP (single nucleotide polymorphism) identification process that are simultaneously detected within the fumC/fimH loci of the bacterium. The disclosure provides a PCR detection kit incorporating a SNP compilation that forms a BFC (Binary Footprint Code) that allows for rapid identification of multiple E. coli clonotypes based on their SNP footprint. Commercial implementation of clonal diagnostics will improve patient care by moving toward personalized medicine strategies, decreasing 'drug-bug' mismatches and exposure to last-line antibiotics, and limiting persistent and severe infections.

The present disclosure provides a binary typing scheme for specific SNP identifications for diagnostic clonotyping that can be adapted for various nucleic acid amplification protocols. Preferably, the nucleic acid amplification protocols are of an isothermal method. More preferably, the present disclosure provides a method for determining which drugs a particular infection will be susceptible to or resistant to, comprising:

(a) obtaining a sample of infecting bacteria;
(b) determining the clonal-type of the infecting bacteria by performing multiplex PCR reactions with SNP-specific primers from binary foot print codes (BFC)-covered clonotypes to determine which SNPs are present or absent; and
(c) matching the results of which SNPs are present or absent to a lookup table for the bacterial species to determine the therapeutic agents the bacteria will be susceptible to or resistant to.

Preferably, the sample of infecting bacteria is taken from a bodily fluid source selected from the group consisting of urine, blood, saliva, tears and a skin swipe. More preferably, the bodily fluid sample is from urine from a patient suspected of a urinary tract infection. Most preferably, the urine sample is first fractionated to separate bacterial components from other nucleic acids, ureas and solids from a urine sample. Preferably, the fractionated bacteria are then lysed to obtain bacterial nucleic acid for further analysis.

Preferably, the multiplex PCR reactions investigate SNPs within a gene loci, wherein the gene is selected from the group consisting of fimbrial adhesin (fimH), fumC, adk, gryB, icd, mdh, purA, recA, and combinations of genes thereof. Preferably, the multiplex PCR reaction utilizes primers to find SNPs in the fimH gene comprising 3'-CACTCAGGGAACCATTCAGGCA-3' (SEQ ID NO. 1) and 5'-CTTATTGATAAACAAAGTCAC-3' (SEQ ID NO. 2). Preferably, the sample is a urine sample from a patient with a urinary tract infection.

The present disclosure further provides a process for typing a sample for clonotyping a clinical sample, comprising:
(a) obtaining a sample of infecting bacteria;
(b) determining the clonal-type of the infecting bacteria by performing multiplex PCR reactions with SNP-specific primers from binary foot print codes (BFC)-covered clonotypes to determine which SNPs are present or absent; and
(c) matching the results of which SNPs are present or absent to a lookup table for the bacterial species to determine the therapeutic agents the bacteria will be susceptible to or resistant to.

BRIEF DESCRIPTION OF THE DRAWINGS

The patent file contains at least one drawing executed in color. Copies of this patent with color drawings will be provided by the Office upon request and payment of the necessary fee.

FIG. 6 shows a majority of clinically significant samples were well below a 22-minute PCR reaction time. When combined with an 8 min-long 1$^{st}$ sample preparation step, it would constitute about 30 minutes to run the whole test. There were few samples from the high-load group that required, surprisingly, longer time for a positive answer (circled in red on the Figure). Some of them were so-called "dirty" samples in that they contained additional substances that interfered with the PCR reaction, making the read-out difficult, thus requiring longer time to process.

Figure 8B:
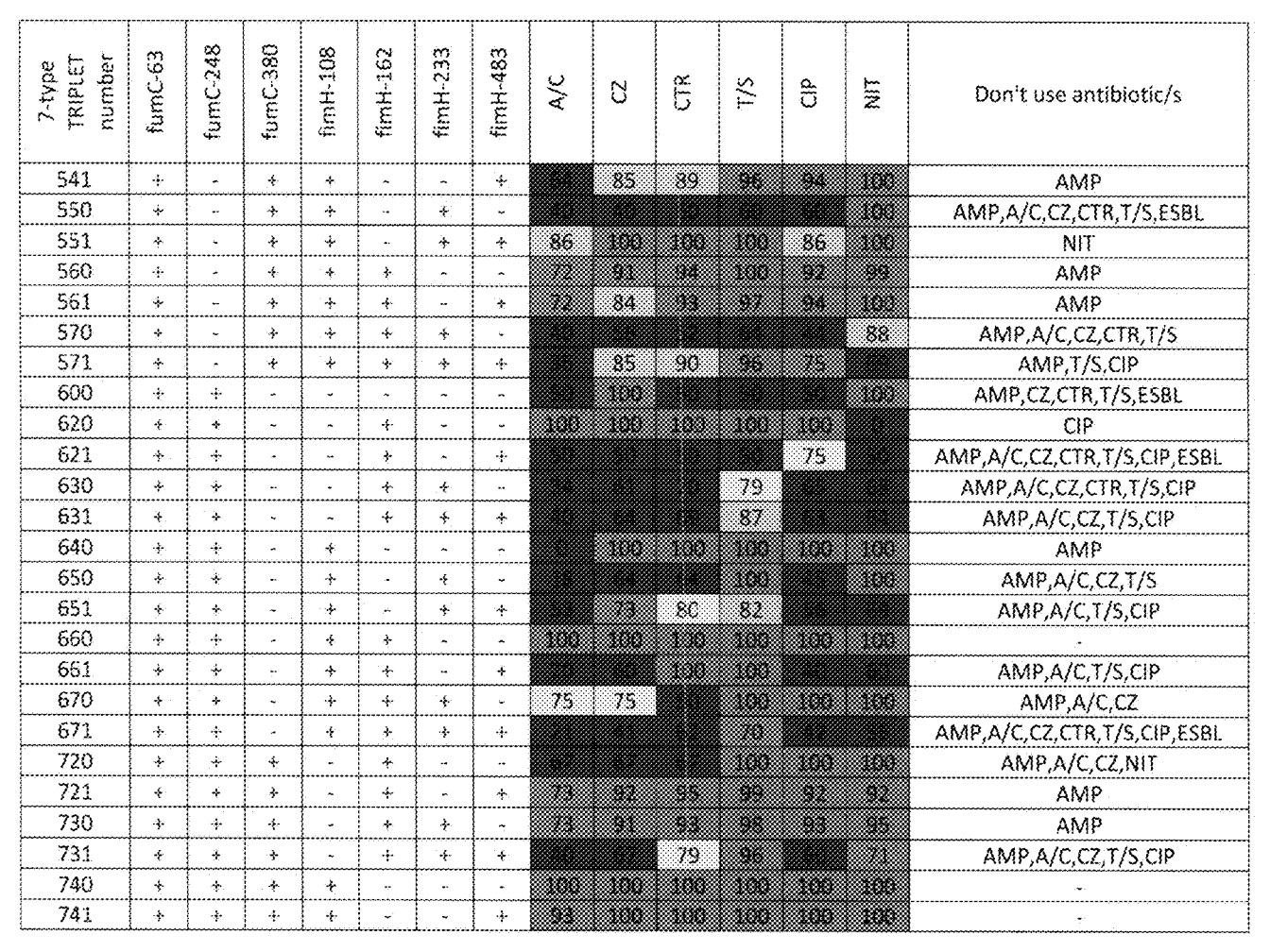

FIGS. 8A-8C show Lookup Table 1, indicating cumulative antibiotic susceptibility of 7-type *E. coli* clonotypes identified according to the present disclosure. Dark green indicates that 90-100% of bacteria of the indicated 7-type are sensitive to the antibiotic. Pale green indicates 80-90% sensitivity. Yellow indicates 75-80% sensitivity. Orange indicates 70-75% sensitivity. Red indicates that more than 30% of bacteria of the indicated 7-type are resistant to the antibiotic.

FIG. 9 shows nucleotide sequence of a 469 bp fragment of *E. coli* fumC (allele 4). Positions of preferred forward primers are indicated in bold letters, and SNP positions are highlighted green and indicated with a number in parentheses.

FIG. 10 shows nucleotide sequence of a 489 bp fragment of *E. coli* fimH (allele 27). Positions of preferred forward primers are indicated in bold letters, and SNP positions are highlighted green and indicated with a number in parentheses.

FIG. 11 shows Table 10, which is a Lookup Table according to the present disclosure that indicates antibiotic profiles of major septatypes from a reference *E. coli* collection.

FIG. 12 shows Table 11, which is a Lookup Table that indicates antibiotic resistance of reference set and field trial *E. coli* isolates.

FIG. 13 shows Table 12, providing prescription rates of, and resistance rates against, the indicated classes of antibiotics in patients diagnosed with *E. coli* infection.

FIG. 14 shows Table 13, which adds to Table 12 the rate of drug-bug mismatches (right hand-most column) in 236 patients treated for *E. coli* with the indicated classes of prescribed antibiotics.

FIG. 15 shows Table 14, which adds to Table 13 the allowance rate of the indicated classes of prescribed antibiotics (right hand-most column), for *E. coli* typed according to a clonotyping test of the present disclosure and based on an antibiotic resistance cutoff value of 15%.

FIG. 16 shows Table 15 which adds to Table 14 the percentage of drug-bug mismatch of *E. coli* isolates versus allowed antibiotics following a clonotyping test of the present disclosure.

DETAILED DESCRIPTION

Figure 1:
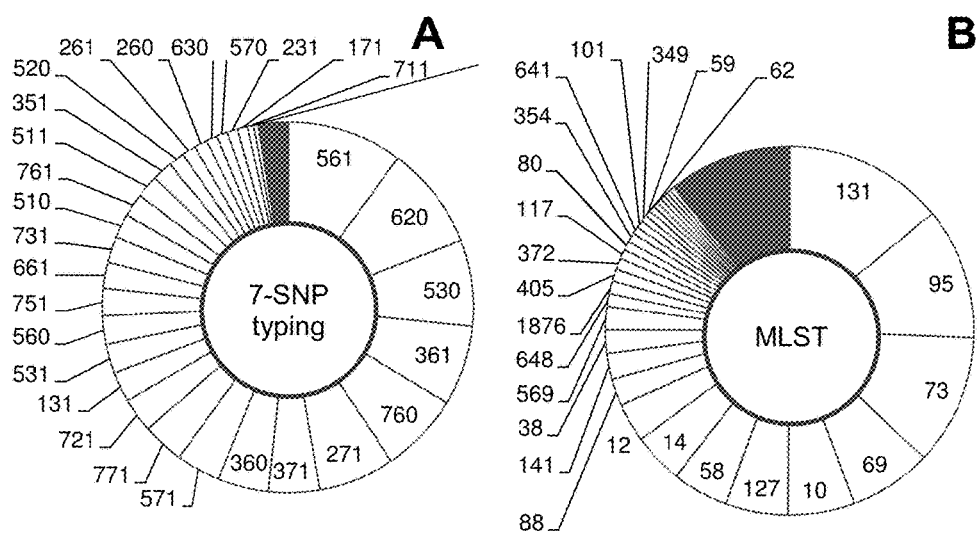
FIG. 1 shows a comparison of diversity detected by the disclosed SNP clonotyping typing process (A) or conventional multi-locus sequence typing (MLST) (B). A reference set of 2,599 clinical E. coli was split into clonotypes using either 7-SNP typing or conventional MLST. The segments of the doughnuts represent individual clonotypes; their size reflects their prevalence within the population. Clonotypes are sorted in descending order of prevalence. All non-minor clonotypes (>0.5% of population) are labeled.

The present disclosure is based on first creating a lookup table by correlating the clonal subtypes of various bacterial isolates, such as *E. coli* isolates with the susceptibility tests achieved for such isolates. There is an urgent need to provide physicians with rapid antimicrobial assays that guide appropriate treatment decisions to minimize the risks associated with inappropriate or ineffective antimicrobial use. In Tchesnokova et al., (*Journal of Clinical Microbiology*, 2013), commercial implementation of clonal diagnostics will improve patient care by moving toward personalized medicine strategies, decreasing 'drug-bug' mismatches and exposure to last-line antibiotics, and limiting persistent and severe infections. However, earlier such studies have used difficult and expensive sequencing techniques to identify clonal subtypes. A clonal differentiation of *E. coli* study was performed by Sanger sequencing, pyrosequencing, or gene-specific real-time PCR, all of which are high-complexity, labor intensive and/or low clonotype-coverage protocols (Niemz et al., *Trends Biotechnol.* 29:240-250, 2011). Instead, the present disclosure provides a simple binary typing scheme that is adopted using established DNA amplification protocols that use simpler instruments (than sequencing) and are suitable for rapid point-of-care use.

Sequences of all primers used in the disclosed 7t method are listed in Table 2. The disclosed kit comprises a combination of Forward and Reverse primers allowed for identification of three SNP's in fumC gene—(1) SNP at position 63, (2) SNP at position 248, (3) SNP at position 380, and four SNP's in fimH gene—(4) SNP at position 108, (5) SNP at position 162, (6) SNP at position 233, (7) SNP at position 488.

A large set (around 2,000) of *Escherichia coli* isolated from independent patients' samples in the last 5 years was used to determine the combination of SNPs (single nucleotide polymorphisms) in two genes (fumC and fimH) that produced the greatest variability and diversity of resulting 7-types.

The same set of *E. coli* was again used to calculate the cumulative antibiotic susceptibility (CAS) of each 7-type to a set of 7 antibiotics representing all major groups of antimicrobials used to treat *E. coli* infections: ampicillin (AMP), amoxicillin/clavulanate (AMC), cefazolin (CZ), ceftriaxone (CTR), trimethoprim/sulfamethoxazole (T/S), ciprofloxacin (CIP) and nitrofurantoin (NIT). Further, each antibiotic for every 7-type was judged as either allowed or rejected for use based on the CAS for this 7-type, e.g., if particular 7-type had CAS<80% to ciprofloxacin, use of fluoroquinolones is not recommended.

TABLE 1

Primer sequences and 5x primer mixes for typing reactions.

| SNP | Forward primer/s, 100 µM stock | V, µl | Reverse primer, 100 µM stock | V, ul | Water to add to 100 µL |
|---|---|---|---|---|---|
| 1 | fumC-63 AGCATGACGAC GAATTCCTGC SEQ ID NO. 5 | 2.5 | GTCGTCGTTAG GGTGAACTTT SEQ ID NO. 6 | 2.5 | 95 |
| 2 | fumC-248 ACGGCGATGCA CGTTGCGTCG SEQ ID NO. 7 | 2.5 | AGTTCCGCTAC GTGAGGCAGG SEQ ID NO. 8 | 2.5 | 95 |
| 3 | fumC-380 CAGGACGCCAC GCCGCTCACG SEQ ID NO. 9 CAGGACGCGAC GCCGCTCACG SEQ ID NO. 11 CAGGATGCGAC GCCGCTCACG SEQ ID NO. 12 | 5 2.5 2.5 | AGTTCCGCTAC GTGAGGCAGG SEQ ID NO. 10 | 5 | 85 |
| 4 | fimH-108 GTGGAGCAAAA CCTGGTCTTG SEQ ID NO. 13 | 5 | AGGGAAAGGAT AGCTACTGCC SEQ ID NO. 14 | 5 | 90 |
| 5 | fimH-162 TATCCGGAAAC CATTACAGAC SEQ ID NO. 15 | 2.5 | TCAAATAAAGC GCCACCGGCC SEQ ID NO. 16 | 2.5 | 95 |
| 6 | fimH-233 TTCCGAGACCG TAAAATATAG SEQ ID NO. 17 | 2.5 | TCAAATAAAGC GCCACCGGCC SEQ ID NO. 18 | 2.5 | 95 |

TABLE 1-continued

Primer sequences and 5x primer mixes for typing reactions.

| SNP | Forward primer/s, 100 µM stock | V, µl | Reverse primer, 100 µM stock | V, ul | Water to add to 100 µL |
|---|---|---|---|---|---|
| 7 | fimH-GTGGTGGCTAC 483 TGGCGGCAGC SEQ ID NO. 19 | 2.5 | TCTGCGGTTGT GCCGGATAGG SEQ ID NO. 20 | 2.5 | 95 |
| 8 | uidA TCTTGCCGTTT con- TCGTCGGTA trol SEQ ID NO. 21 | 2.5 | CACGCCGTATG TTATTGCCG SEQ ID NO. 22 | 2.5 | 95 |

An expanded fumC/fimH sequence database containing defined major clonotypes of interest, determines a Binary Footprint Codes BFCs, by using an algorithm designed specifically for clonotype calling based on unique combination of informative SNPs. The candidate barcode loci are provided for determining optimally predictive BBCs by using a proprietary script using the following general algorithm. To extract a BBC with high-resolution power, all candidate SNPs are considered as specific 'features'. The goal is to select 6-10 features with a sufficiently large number of binary (presence/absence) combinations to distinguish all or, at least, the most resistant diagnostic clonotypes. This fits as a problem in statistical pattern recognition, with a goal to represent existing patterns in the reduced number of dimensions (i.e., features). The first step is feature selection using a filter method to produce loci with the highest variance (resolving ability) between all clonotypes (n), with 2/n the lowest and n/2 the highest value possible. The method employs principal component analysis, calculating variance of each feature in binary form (gene or SNP presence/absence). The second step follows the wrapper method where the learning algorithm is wrapped into the selection of the best candidate that is maximally unlinked to any other feature already chosen. If a selected feature has more than two possibilities (e.g., A/C/G in same nucleotide position), the one with the best resolving power will be considered.

Figure 3:
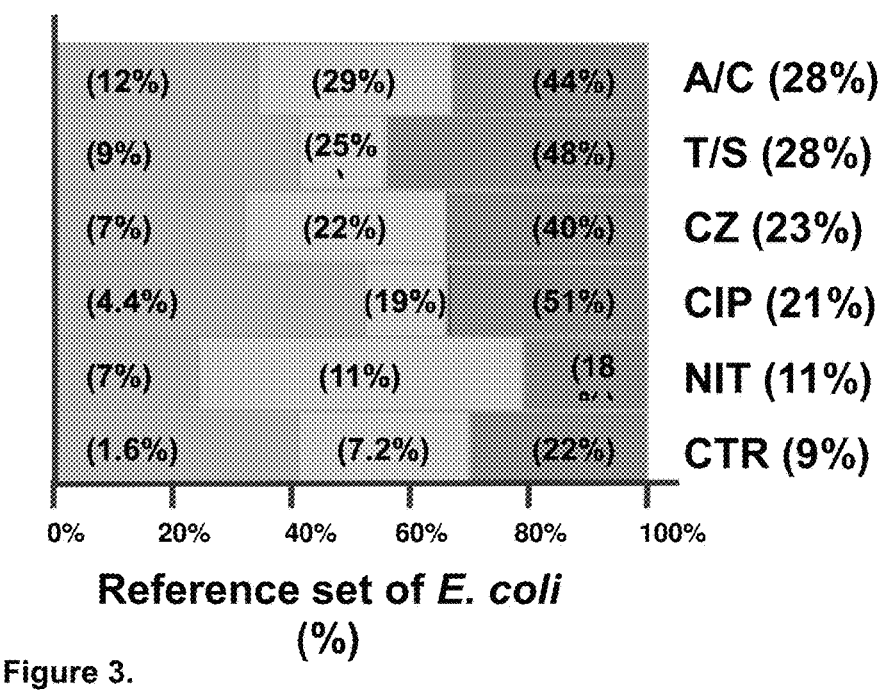
FIG. 3 shows a 7-SNP typing-based detection of taxa with divergent antimicrobial resistance phenotypes. The reference set of 2,599 Escherichia coli isolates was analyzed as shown in FIG. 2, namely, 7-SNP typing was used to split the set into individual clonotypes, for which the level of resistance prevalence to a set of tested antibiotics was calculated. Each bar represents the whole reference set of isolates analyzed by 7-SNP typing. Each bar is split into three areas: isolates belonging to clonotypes which have significantly lower than average resistance prevalence to an antibiotic (green), to clonotypes with significantly higher resistance prevalence than the average (red), and to clonotypes with resistance prevalence not statistically different from the average (grey). Numbers in parentheses denote the level of antibiotic resistance prevalence within a respective fraction. Antibiotics are listed on the right side of the graph with the respective average resistance prevalence within the reference set (A/C, amoxicillin/clavulanate, T/S, trimethoprim/sulfamethoxazole, CZ, cefazolin, CIP, ciprofloxacin, NIT, nitrofurantoin, CTR, ceftriaxone).

Variable SNPs are based on CH clonotyping, such as on fumC/fimH sequence information. Thus, we select limited combinations of SNPs that allow a binary approach (that is, SNP presence/absence) used to identify different clonotypes based on their unique SNP combinations. To adapt the test for use with standard strip tubes, one can select as few as 8 informative SNPs to comprise BFCs, which contain enough unique SNP combinations (up to 256) to distinguish most or, at least, a good portion of clonotypes from each other. The BFC is adapted for 8 single-plex or, as few as 2 four-plex reactions (i.e. 8 or 2 tube strips). FIG. 3 shows BFCs for the 20 major clonotypes.

SNP-specific primers are designed to identify the selected SNPs at CH clonotyping gene regions, that are suitable for use in alternative isothermal amplification protocols (as well as RT-PCR). One preferred method is a loop-mediated isothermal amplification (LAMP) protocol that includes 2 or 3 layers (depending on the number of primer pairs used) of specificity control. It is also very robust and can use colorimetry (double-stranded DNA dyes) and/or simple turbidity ($Mg_2P_2O_7$ precipitation) for the reaction read-out. Other isothermal amplification methods include recombinase polymerase amplification (RPA) and helicase-dependent amplification (HAD). Both methods utilize colorimetry for detection, using essentially the same instrumentation platforms as LAMP.

Lookup Table

Positive (+) or negative (−) amplification indicates at the presence or absence of specific SNP. Combination of presence/absence data for all 7 SNP's provides unique 7-type (first column on the left). Each 7-SNP type is assigned the probability of an isolate that belongs to it to be sensitive or resistant to different antibiotics on a scale from 0 to 100, with 0 being completely resistant and 100 being completely sensitive. If 90-100% bacteria that belong to this 7-SNP type are sensitive to particular antibiotic, the respective cell in the Lookup Table is colored green, and this antibiotic is recommended to be used for treatment; pale green indicates 80-90% sensitivity level, and treatment is allowed too. Yellow (75-80%) and orange (70-75%) indicate that treatment is still allowed but with caution, and switching to a different antibiotic is recommended. Red indicates that more than 30% of bacteria are resistant to this antibiotic, and the latter should be rejected as a choice for treatment. Six representatives of most widely used classes of antibiotics are listed in the Table: A/C, amoxicillin/clavulanate, CZ, cefazolin ($1^{st}$ generation cephalosporin), CTR, ceftriaxone ($3^{rd}$ generation cephalosporin, bacteria resistant to it tend to produce ESBL's), T/S, trimethoprim sulfamethoxazole, CIP, ciprofloxacin (fluoroquinolones), and NIT, nitrofurantoin.

Primers are designed for both single-plex (8 tubes; suited for one-channel, no-probe platforms) and multiplex (<8 tubes; for multi-channel/-probes platforms) kit options. Specificity of the designed SNP-specific primers are evaluated first using selected representatives of clonotypes included in the assay (1-3 isolates each, up to 100 total) to ensure they prime as expected. Primers that pass these initial screens are validated more extensively by using a wide range of clinical isolates (up to 2,000), representing the BFC-covered clonotypes and more, to rigorously test primer specificity and sensitivity. Bacterial DNA isolation from urine was performed by using commercial methods, based on chelex beads, pore filters, or columns.

Although the primer testing results can be evaluated by naked eye (based on turbidity) or using UV-light (SYBR-Green dye), additional instruments are an ESE-Quant Tube Scanner (Qiagen, Inc). Additionally, a Genie II™ (Pro-Lab Diagnostics, Inc.) is a multi-functional, one-channel isothermal platform accommodates two 8-well strips for single-plex reactions, or a Rotor-Gene Q instrument for RT-PCR tests.

The disclosure provides a rapid molecular diagnostics test kit that allows high-resolution clonal (sub-species) typing of E. coli that cause urinary tract infection (UTI)—cystitis, pyelonephritis, and urosepsis. The clonotyping test is used for prediction of antibiotic resistance of the bacteria and will be based on a proprietary compilation of clonotyping markers—fumC and fimH gene loci, and a binary SNP-typing technology. In a preferred embodiment, PCR 8-12 tube strips are functionalized for simultaneous detection of the presence/absence of multiple single nucleotide polymorphisms (SNPs) within fumC/fimH loci. These specific SNPs set comprise Binary Barcode Combination (BBC) that allows identification of a large number of E. coli clonal lineages (clonotypes) based on their unique sequence footprints (see FIG. 1).

We have designed and validated (by PCR) BBC comprised of 7 SNPs that can be used in 8-tube strip single-plex configuration and allows separation of *E. coli* on 56 clonotypes. These are the *E. coli* fumC gene (SEQ ID NO. 3) at least at positions 63, 248, 380, and combinations thereof, and the fimH gene (SEQ ID NO. 4) at least at positions 108, 162, 233, 483, and combinations thereof. The BBCs are used in a rapid test based on Real-Time (RT-) PCR or isothermal (isoT) amplification instrumentation platforms in on-site clinical laboratories in/nearby emergency rooms, urgent care clinics and hospitals. The test is performed directly on the clinical specimen (patient urine), in a timely (<30 min) manner.

Preferably, the multiplex PCR reaction detects compilations of SNPs at the *E. coli* fumC gene (allele 4, 469 bp fragment; SEQ ID NO:3) (FIG. 9) and the
fimH gene (allele 27, 489 bp fragment; SEQ ID NO. 4) (FIG. 10).

Example 1

This example shows a method for using the disclosed kit to test a sample for clonotyping an *E. coli* sample to determine antibiotic susceptibility.
1) Prepare 8 master mixes for qPCR (see Tables 1 and 2)
2) Add 1 µl of template DNA to 9 µl of master mix solution of each 8 reaction
3) Run qPCR reaction of Rotorgene® Q instrument as follows:
   1. 3 min denaturation at 95° C.
   2. 5 sec at 95° C.
   3. 5 sec at 57° C.
   4. 10 sec at 72° C. (acquisition at green channel)
   5. Repeat steps 2-4 40 times
   6. Perform HRM (high resolution melt) over 70-90° C. range
4) Analyze resulting curves and melting peaks to assign positive or negative result
5) Determine resulting 7-type and lookup the respective CAS in the Lookup Table.

TABLE 2

Master mix for 7-type qPCR

| Reagent | Volume per 1 reaction, uL | Volume per X reactions, uL |
|---|---|---|
| 2x SYBR Green Reagent buffer (Qiagen) | 5 | |
| Primer mix, 5x (per Table 2) | 2 | |
| DNA (to add last) | 1 | |
| Water, to add to 10 µl | 2 | |

Example 2

This example illustrates a high-resolution fumC/fimH (CH) clonotyping scheme for *E. coli* based on sequence variations within these highly-variable omnipresent genes for fumarase and fimbrial adhesin of *E. coli*, respectively. We correlated CH clonotypes with antibiotic susceptibility profiles among 1,600 urine *E. coli* isolates from clinical microbiology laboratories in Seattle (Group Health, UW, Harborview, and Children's Hospitals), Minneapolis (VA Medical Center), and Munster, Germany (University Clinic).

Figure 2:
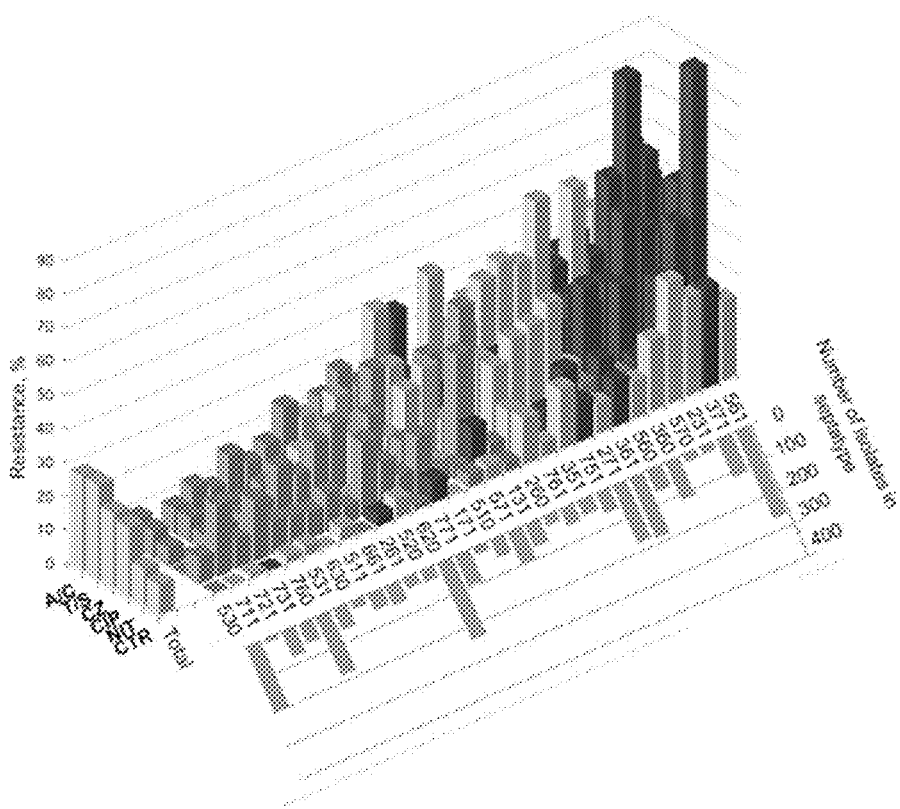
FIG. 2 shows a clonotype-specific antibacterial resistance profile. The reference set of 2,599 Escherichia coli isolates was split into septatypes by computer sequence analysis. The prevalence of resistance within individual non-minor septatypes (>0.5% of isolates each) to amoxicillin/clavulanate (A/C), trimethoprim/sulfamethoxazole (T/S), cefazolin (CZ), ciprofloxacin (CIP), nitrofurantoin (NIT), and ceftriaxone (CTR) is plotted as vertical columns. Columns are colored-coded to indicate whether, compared with the total population, the prevalence of resistance in this clonotype is significantly ($P<0.05$) higher (red) or lower (green), or is not significantly different (gray). The graph inserted to the lower right of the main graph shows the number of isolates in individual septatypes.

A total of 222 distinct CH clonotypes were identified, with the top 20 clonotypes comprising two-thirds of isolates (FIG. 1). Importantly, within each of the major clonotypes the prevalence of resistance differed by 2-fold (higher or lower) from the overall population value for at least one antimicrobial (FIG. 2). Additionally, clonotype resistance was similar (stable) across all laboratories.

We next determined how knowledge of cumulative clonotype vs. overall (species) antibiogram could reduce potential 'drug-bug' mismatches during empirical antibiotic selection. We used the IDSA-recommended 80% susceptibility cutoff level to allow the use of specific antibiotic for each clonotype. Among the top 4 antibiotics used against *E. coli*-fluoroquinolones (CIP), trimethoprim-sulfamethoxazole (T/S), cefazolin (CZ), and amoxicillin-clavulanate (A/K)—the drug allowance coverage is 48-79% and potential decrease in drug-bug mismatch 45% to 78%, if the empirical choice is guided by the clonotyping, not species identity alone (Table 3).

TABLE 3

Decrease in potential 'drug-bug' mismatch based on CH clonotyping of *E. coli* (as % resistant in 'Allowed' for treatment vs. total resistant).

| | | Clonotype-based treatment choice | | |
|---|---|---|---|---|
| Antibiotic | Total resistant | % Rejected/ % Resistant | % Allowed/ % Resistant | Improvement |
| T/S | 26.9% | 42.0/50.1 | 58.0/10.1 | 62.4% |
| A/K | 25.5% | 51.9/36.5 | 48.1/13.5 | 46.8% |
| CZ | 19.7% | 42.0/32.0 | 58.0/10.7 | 45.4% |
| CIP | 17.1% | 20.6/68.7 | 79.4/3.7 | 78.1% |

Example 3

This example illustrates implementation of clonal testing in a healthcare community microbiology laboratory. We assessed the presence of *E. coli* sub-strains ST131 and ST69 (n=619) *E. coli* positive cultures. Antibiotic resistance of these two clonotypes is distinctive from *E. coli* in general with greater than 40% resistant to trimethoprim/sulfamethoxazone (TMS) (ST69 and ST131) and fluoroquinolonwa (FQ) for ST131. The tests were conducted to identify ST69 of ST131 genes specific to each clonotype on bacterial DNA isolated from patient urine specimens using RT-PCR instrumentation. The entire test protocol took 45-90 minutes to run and detected down to $10^2$ cfu/ml of urine, with specificity and sensitivity of greater than 95%. The overall prevalence of the two clonotypes was 15% of the total samples with ST131 at 10.2% (63/619) and ST69 at 5.0% (31/619). Table 4 shows the age and gender distribution of the study group by *E. coli* clonal status and the study group was primarily women. Patients with ST131 infection were generally older (75% were age 60 or older).

TABLE 4

| Age | Entire Cohort (n = 619) | ST69 (n = 32) | ST131 (n = 63) |
|---|---|---|---|
| 18-30 | 13% | 19.4% | 9.5% |
| 31-40 | 10.3% | 13% | 3% |
| 41-50 | 9.5% | 13% | 6.3% |
| 51-60 | 14.7% | 3.2% | 6.3% |
| 61-70 | 18% | 13% | 20.6% |
| 71-80 | 14.5% | 9.7% | 22% |
| 81-90 | 16% | 16.1% | 25.4% |
| 91-100 | 3.7% | 12.9% | 6.3% |
| male | 8.1% | 6.5% | 11% |
| female | 92% | 93.5% | 88.9% |

In the study group, 36% were treated with TMS and 36% were treated with FQs. Resistance to TMS was 15% and resistance to FQs was 11% (FIG. 3). Overall, 8% of patients were prescribed antibiotic therapy for which the isolate was resistant (a drug-bug mismatch). However, the treatment mismatch was significantly higher in patients infected with either ST69 of ST131, 17% and 22%, respectively. ST69 and ST131 together comprised 40% (19/48) of patients with drug-bug treatment mismatch. In 18% (113/619) patients, the initial antibiotic treatment course was changed (switched). Treatment switching occurred in 34% of patients infected with ST69 and 41% of patients of those infected with ST131. These two clonotypes together comprised 33% of all treatment switch cases.

Only 20% of patients who were treated with the correct antibiotic has a follow-up encounter. Almost 90% of patients with a drug-bug mismatch had a follow-up. Overall, drug-bug mismatches contributed to 28% of all follow-up encounters. These data show that a correction of the original antibiotic treatment based on fast diagnosis of ST69 of ST131 would potentially reduce overall drug-bug mismatches by 37%, resulting in 2.6 fewer follow-ups per 100 patients. Further, if the disclosed test kit and process were used for all major clonotypes, the reduction in drug-bug mismatch would be 63%, resulting in 4.4 fewer follow-up per 100 patients.

Example 4

This example illustrates setting up a reference database consisting of 2,559 random single-patient clinical *E. coli* isolates of primarily extra-intestinal origin, at eight international clinical microbiology laboratories. The major source of isolates was urine (67.1%), followed by feces (6.8%) and blood (4.6%), with the rest of isolates originating from wound, abdominal and other swabs of extra-intestinal compartments. Conventional MLST (multi-locus sequence typing) was performed either in full using the standard scheme of 7 MLST loci (adk, fumC, gyrB, icd, mdh, purA, and recA) (Wirth et al., 2006. Sex and virulence in *Escherichia coli*: an evolutionary perspective. Mol. Microbiol, 60:1136-1151.) or as a combination of partial MLST and fumC/fimH typing, as described previously (Tchesnokova et al. 2013. Predictive diagnostics for *Escherichia coli* infections based on the clonal association of antimicrobial resistance and clinical outcome. J. Clin. Microbiol. 51:2991-2999). Some ST complexes, as identified by the eBURST v3 software, were defined operationally as a single 'ST' and were designated based on the ST identified as the cluster's founder (see Table 5) (Feil et al. 2004. eBURST: inferring patterns of evolutionary descent among clusters of related bacterial genotypes from multilocus sequence typing data. J. Bacteriol. 186:1518-1530). Such complexes accounted collectively for 17.5% of isolates, with most comprised of minor groups.

Table 5 shows the composition of septatypes. All 54 septatypes identified within the 2,599 *E. coli* clinical isolates are listed in the table in the descending order according to their size. Within each septatype two major ST-H subclones and major phylogroups are listed if they comprise at least 5% of a septatype. Homogenous major septatypes which consist of primarily (more than 89%) of one ST-H subclone are in bold.

TABLE 5

| Septatype | | Major ST (H) subclones | | | | Prevalent phylogroups | | | |
| --- | --- | --- | --- | --- | --- | --- | --- | --- | --- |
| | | First | | Second | | First | | Second | |
| Name | %$^a$ | Name | %$^b$ | Name | %$^b$ | Name | %$^b$ | Name | %$^b$ |
| Major septatypes (>0.5% of the population) | | | | | | | | | |
| 561 | 10.1 | ST131 (H30) | 95 | na | <5 | B2 | 99.2 | na | <5 |
| 620 | 9.0 | ST73 (H9/10) | 97.8 | na | <5 | B2 | 100 | na | 0 |
| 530 | 7.6 | ST127 (H2) | 73.2 | ST141 (H14) | 15.1 | B2 | 96 | na | <5 |
| 361 | 7.0 | ST58 (H32/31)$^c$ | 23.9 | ST354 (H58) | 10.8 | B1 | 50 | F | 19.6 |
| 760 | 6.9 | ST95 (H41) | 90 | na | <5 | B2 | 90.7 | na | <5 |
| 271 | 6.7 | ST69 (H27) | 92.8 | na | <5 | D | 100 | na | 0 |
| 371 | 4.4 | ST88 (H23/27)$^d$ | 25.2 | ST58 (H25/27) | 23.3 | B1 | 35 | C | 24.8 |
| 360 | 4.4 | ST58 (H38/86)$^c$ | 34.1 | ST88 (H39) | 13.2 | B1 | 62.1 | C | 14.7 |
| 571 | 3.8 | ST14 (H27/64)$^d$ | 97.1 | na | <5 | B2 | 100 | na | 0 |
| 771 | 3.6 | ST10 (H23/27)$^e$ | 51.3 | ST95 (H27) | 45.8 | A | 52.1 | B2 | 47.9 |
| 721 | 3.0 | ST95 (H15) | 93.9 | ST10 (H15) | 5.2 | B2 | 93.7 | A | 6.3 |
| 131 | 2.62 | ST12 (H5) | 92.7 | na) | <5 | B2 | 100 | na | 0 |
| 531 | 2.54 | ST141 (H5) | 43.1 | ST491 (H5) | 15.3 | B2 | 94 | na | <5 |
| 560 | 2.51 | ST131 (H41) | 100 | na | <5 | B2 | 100 | na | <5 |
| 751 | 2.39 | ST10 (H54) | 75 | ST95 (H54) | 8 | A | 81 | B2 | 17.5 |
| 661 | 2.28 | ST73 (H30) | 92.7 | na | <5 | B2 | 100 | na | 0 |
| 731 | 2.28 | ST569 (H5) | 90 | na | <5 | B2 | 93.3 | na | <5 |
| 510 | 2.09 | ST131 (H22) | 89.3 | ST428 (H22) | 8.9 | B2 | 100 | na | 0 |
| 511 | 2.01 | ST1876 (H20/21) | 56.8 | ST429 (H20) | 20.9 | B2 | 100 | na | 0 |
| 761 | 2.01 | ST10 (H30/31) | 41.8 | ST95 (H30) | 35.7 | A | 43.4 | B2 | 37.7 |
| 351 | 1.71 | ST69 (H54) | 28.9 | ST58 (H54) | 20 | D | 44.4 | B1 | 24.4 |
| 520 | 1.40 | ST372 (H9/12) | 70.3 | ST636 (H9/75) | 8.1 | B2 | 100 | na | 0 |
| 261 | 1.21 | ST69 (H47) | 28 | ST394 (H35/47) | 21.9 | D | 90.6 | na | <5 |
| 260 | 1.14 | ST38 (H65) | 43 | ST59 (H41) | 30 | D | 70 | F | 30 |
| 570 | 0.95 | ST117 (H97) | 89.2 | na | <5 | F | 92 | na | <5 |
| 630 | 0.95 | ST80 (H1) | 84 | ST73 (H2/154) | 16 | B2 | 100 | na | 0 |

TABLE 5-continued

| Septatype | | Major ST (H) subclones | | | | Prevalent phylogroups | | | |
| --- | --- | --- | --- | --- | --- | --- | --- | --- | --- |
| | | First | | Second | | First | | Second | |
| Name | %[a] | Name | %[b] | Name | %[b] | Name | %[b] | Name | %[b] |
| 231 | 0.91 | ST38 (H5) | 100 | na | 0 | D | 100 | na | 0 |
| 171 | 0.87 | ST12 (H27) | 100 | na | 0 | B2 | 100 | na | 0 |
| 711 | 0.53 | ST676 (H21) | 43 | ST2551 (H20) | 21 | B2 | 100 | na | 0 |
| Minor septatypes (<0.5% of the population) | | | | | | | | | |
| 350 | 0.42 | ST405 (H56) | 91 | ST2711 (H111) | 9 | D | 90.9 | Clade I | 9.1 |
| 551 | 0.27 | ST144 (H54) | 57 | ST2086 (H57) | 43 | B2 | 100 | na | 0 |
| 330 | 0.19 | ST58 (H2) | 40 | ST2250 (H2) | 20 | B1 | 40 | Clade I | 40 |
| 331 | 0.19 | ST648 (H5) | 60 | ST38 (H5) | 20 | F | 60 | na | <5 |
| 550 | 0.19 | ST2015 (H197) | 100 | na | 0 | B2 | 100 | na | 0 |
| 160 | 0.15 | ST12 (H41) | 50 | ST1011 (H108) | 25 | B2 | 50 | Sh-I | 25 |
| 251 | 0.15 | ST38 (H54) | 25 | ST69 (H54) | 25 | D | 75 | F | 25 |
| 321 | 0.15 | ST58 (H15) | 25 | ST648 (H15) | 25 | F | 50 | B1 | 25 |
| 370 | 0.15 | ST991 (H123) | 25 | ST1882 (H123) | 25 | D | 75 | B1 | 25 |
| 651 | 0.15 | ST706 (H229) | 50 | ST73 (H54) | 50 | B2 | 100 | na | 0 |
| 671 | 0.15 | ST73 (H27) | 25 | ST706 (H25) | 25 | B2 | 100 | na | 0 |
| 720 | 0.11 | ST2622 (H75) | 67 | ST2474 (H9) | 33.3 | B2 | 100 | na | 0 |
| 730 | 0.11 | ST73 (H154) | 33.3 | ST1444 (H3) | 33.3 | B2 | 66.7 | Clade I | 33.3 |
| 300 | 0.08 | ST2141 (H0) | 50 | ST2711 (H0) | 50 | F | 50 | Clade I | 50 |
| 611 | 0.08 | ST583 (H21) | 100 | na | 0 | B2 | 100 | na | 0 |
| 710 | 0.08 | ST803 (H88) | 100 | na | 0 | B2 | 100 | na | 0 |
| 200 | 0.08 | ST59 (H0) | 100 | na | 0 | F | 100 | na | 0 |
| 121 | 0.04 | ST12 (H15) | 100 | na | 0 | B2 | 100 | na | 0 |
| 220 | 0.04 | ST73 (H10) | 100 | na | 0 | B2 | 100 | na | 0 |
| 221 | 0.04 | ST38 (H15) | 100 | na | 0 | D | 100 | na | 0 |
| 310 | 0.04 | ST399 (H22) | 100 | na | 0 | C | 100 | na | 0 |
| 320 | 0.04 | ST10309 (H9) | 100 | na | 0 | Clade I | 100 | na | 0 |
| 500 | 0.04 | ST636 (H0) | 100 | na | 0 | B2 | 100 | na | 0 |
| 521 | 0.04 | ST636 (H15) | 100 | na | 0 | B2 | 100 | na | 0 |
| 660 | 0.04 | ST73 (H41) | 100 | na | 0 | B2 | 100 | na | 0 |

[a] Percent of the *E. coli* population within a septatype
[b] Percent of ST-H subclone of a phylogroup within a septatype
[c] These are not individual STs but subgroups of several linked STs identified by Eburst software. The ST listed in the table is the primary subgroup founder, whereas the actual composition of this subgroup is as follows (individual STs are listed according their size in descending order; STs that contain only 1-2 isolates are not listed): (1) ST58 (13 isolates out of 50 total within this ST58 (H32/31) subgroup), ST162 (11 out of 50), ST1056 (5 out of 50), ST155 (4 out of 50), ST448 (4 out of 50), ST533 (3 out of 50), etc.; (2) ST224 (14 isolates out of 40 total within this ST58 (H38/86) subgroup), ST297 (12 out of 40), ST58 (3 out of 40), ST155 (3 out of 40), etc.; (3) ST10 (34 isolates out of 50 total within this ST10 (H23/27) subgroup), ST617 (6 out of 50), ST93 (5 out of 50), etc.
[d] Each of these is a complex of three STs which differ by only one MLST allele out of seven (so called single-locus variants, or SLVs, identified by Eburst software). The ST listed in the table is the primary subgroup founder (identified by Eburst), whereas the actual composition of this subgroup is as follows (individual STs are listed according their size in descending order: (1) ST410 (18 isolates out of 29 total within this ST88 (H23/27) complex), ST90 (6 out of 29), ST88 (5 out of 29); (2) ST404 (50 isolates out of 98 total within this ST14 (H27/64) complex), ST1193 (34 out of 98), ST14 (14 out of 98).

fumC and fimH were selected as the gene targets for development of the SNP-based *E. coli* clonotyping method because of the previously demonstrated power of fumC/fimH clonotyping to predict ST-based clonal groups and subdivide them into smaller subclones. To guide SNP selection, a proprietary algorithm was used to select seven SNPs that included 3 SNPs from fumC (positions 63, 248, and 380) and 4 from fimH (positions 108, 162, 233, and 483). The 7-SNP format allowed the test performance in PCR using 8-tube/-well configuration, with the eighth tube or well used for a control. The 7 SNPs were split into three groups. The first group included three SNPs (fumC-63, fumC-248, fumC-380), the second group another three SNPs (fimH-108, fimH-162, fimH-233), and the third group the remaining SNP (fimH-483). Presence of the 1$^{st}$ SNP within a group was scored as 1, presence of the 2$^{nd}$ SNP as 2, and presence of the 3$^{rd}$ SNP as 4, while SNP absence was scored as 0. Each isolate was assigned a score based on the sum of the scores for each SNP group (Table 6). For example, the 101-011-1 binary combination (where '1' and '0' is SNP presence and absence, respectively) was recorded as "561", 010-111-0 as "270", etc.

Table 6 shows scoring of the septatype index scored. 7 SNPs were divided into two groups of 3 SNPs and one group of 1 SNP. When the SNP was present at positions 1 or 4, it was scored a numerical value of 1, at positions 2 or 5 it was scored 2, and at positions 3, 6 or 7 it was scored 4. Scores were summed within groups resulting in a three-digit septatype index.

TABLE 6

| | Gene | | | | | | |
| --- | --- | --- | --- | --- | --- | --- | --- |
| | fumC | | | fimH | | | |
| | SNP # | | | | | | |
| | 63 | 248 | 380 | 108 | 162 | 233 | 483 |
| SNP position | 1 | 2 | 3 | 4 | 5 | 6 | 7 |
| Numerical key assigned if SNP is present | 1 | 2 | 4 | 1 | 2 | 4 | 1 |
| Numerical key assigned if SNP is absent | 0 | 0 | 0 | 0 | 0 | 0 | 0 |

TABLE 6-continued

| | Gene | | | | | | |
|---|---|---|---|---|---|---|---|
| | fumC | | | fimH | | | |
| | SNP # | | | | | | |
| | 63 | 248 | 380 | 108 | 162 | 233 | 483 |
| Example A: CH40-30 (ST131) belongs to septatype 561 | | | | | | | |
| SNP present? | yes | no | yes | no | yes | yes | yes |
| Binary code | 1 | 0 | 1 | 0 | 1 | 1 | 1 |
| Numerical key assigned | 1 | 0 | 4 | 0 | 2 | 4 | 1 |
| septatype number | | 5 | | | 6 | | 1 |
| Example B: CH35-27 (ST69) belongs to septatype 271 | | | | | | | |
| SNP present? | no | yes | no | yes | yes | yes | yes |
| Binary code | 0 | 1 | 0 | 1 | 1 | 1 | 1 |
| Numerical key assigned | 0 | 2 | 0 | 1 | 2 | 4 | 1 |
| septatype number | | 2 | | | 7 | | 1 |

For the 7-SNP clonotyping test, 7 primer pairs were designed and optimized to detect the SNPs, with uidA locus-specific primers added as an *E. coli* positive control (Table 7). The performance of the primers was tested using isolates known to contain fumC and fimH variant alleles with any polymorphisms in the primer-binding region identified in our reference set of 2,559 *E. coli* (Table 7). Primer sequences and product length of seven SNP-specific reactions and uidA *E. coli*-specific control.

TABLE 7

| SNP name | Primer sequence (5'-3')[a] | Product length (bp)[b] |
|---|---|---|
| fumC-63 | (F) AGCATGACG ACGAATTCCTGC | |
| | (R-S) GTCGTCGT TAGGGTGAACTTT SEQ ID NO. 5 | 149 |
| | (R-M) same as fumC-248 (R-S) | 423 |
| fumC-248 | (F) ACGGCGATG CACGTTGCGTCG SEQ ID NO. 7 | |
| | (R-S) AGTTCCGC TACGTGAGGCAGG SEQ ID NO. 8 | 239 |
| | (R-M) same as (R-S) | 239 |
| fumC-380[c] | (F) CCGGAAATCT CCTGCCCAAGC | |
| | (R-S) CATTCCGC AGCTTAAAACCCT | 121 |
| | (R-M) same as (R-S) | 121 |
| fimH-108 | (F) GTGGAGCAAA ACCTGGTCTTG | |
| | (R-S) AGGGAAAG GATAGCTACTGCC | 168 |
| | (R-M) same as fimH-233 (R-S) | 241 |
| fimH-162 | (F) TATCCGGAAA CCATTACAGAC | |
| | (R-S) same as fimH-233 (R-S) | 187 |
| | (R-M) same as fimH-233 (R-S) | 187 |
| fimH-233 | (F) TTCCGAGACC GTAAAATATAG | |
| | (R-S) TCAAATAA AGCGCCACCGGCC | 116 |
| | (R-M) same as fimH-483 (R-S) | 396 |
| fimH-483 | (F) GTGGTGGCTA CTGGCGGCAGC | |
| | (R-S) TCTGCGGT TGTGCCGGATAGG | 146 |
| | (R-M) same as (R-S) | 146 |
| uidA | (F) TCTTGCCGTT TTCGTCGGTA | |
| | (R-S) CACGCCGT ATGTTATTGCCG | 129 |
| | (R-M) same as (R-S) | 129 |

[a]R-S, reverse primer used in singleplex reaction; R-M, reverse primer used in multiplex reaction; singleplex refers to both conventional PCR and qPCR.
[b]Length of PCR product for singleplex and multiplex reaction is denoted in respective rows.
[c]Primers specific for the fumC-380 SNP are designed for the antisense DNA strand; all other primers are designed for the sense DNA strand.

Testing was done in three different formats: singleplex or multiplex conventional PCR, or singleplex qPCR. Singleplex 7-SNP typing consisted of 8 independent reactions using the above-described primers. Multiplex 7-SNP typing used some of the primer pairs combined into three total reactions, as shown in Table 7. The first triplex reaction contained three SNP-specific forward primers (fumC-63, fumC-248, and fimH-483) and two common reverse primers (one each for fumC and fimH). The second triplex reaction contained the uidA primers, two SNP-specific forward primers (fimH-108 and fimH-162), and a common reverse primer for fimH. The duplex reaction contained the same two primer pairs as used in single-plex PCR (for fumC-380 and fimH-233).

Of the 582 isolates that represented fumC/fimH diversity that were used to test primer performance, 310 underwent full 7-SNP typing test (including the uidA control), which was done using a single format for 180 isolates, two formats for 121 isolates, and all three formats for 24 isolates. The remaining 272 test isolates were screened using primers for individual SNPs. If the SNP test failed to detect correct septatype of a particular fimH or fumC allele, the test was repeated to confirm or refute this failure.

Test reactions used JumpStart PCR master mix (Sigma) and the following conditions: 2 min initial denaturation at 95° C., followed by 27 cycles of 15 seconds at 95° C., 15 seconds at 57° C., and 30 seconds at 72° C. Amplification products were analyzed by 2% agarose gel electrophoresis. The qPCR 7-SNP typing test was performed by real-time quantitative PCR on a Rotor-Gene® Q MDx instrument (QIAGEN) using the SYBR-Green PCR Kit (QIAGEN). Unless stated otherwise, the qPCR reaction conditions were as follows: 3 min at 95° C., followed by 30 cycles of 5 seconds at 95° C., 10 seconds at 57° C., and 10 seconds at 72° C., with signal acquisition at the elongation step. As in the singleplex test, the qPCR 7-SNP typing test consisted of 8 independent reactions.

7-SNP typing of *E. coli* from urine samples. To validate the performance of the 7-SNP typing test, 160 random urine samples were obtained from the clinical microbiology laboratory at the Harborview Medical Center (Seattle, Wash.). Each sample was processed as follows: 1 mL urine was added to 50 µL of a 20% suspension of Chelex (BioRad) in sterile water and centrifuged 1 min at 12,000 rpm. The pellet with Chelex was re-suspended in 100 µL of sterile water, heated for 5 min at 96° C. and centrifuged again, with the supernatant used as template for the qPCR-based 7-SNP typing test. The load of *E. coli* in urine was determined from the uidA threshold cycle based on a standard calibration curve (there were no uidA signal in sterile urine samples). In parallel, 10 µL of urine were plated on McConkey agar to detect the growth of *E. coli*. Cultured *E. coli* isolates were further subjected to clonotyping as a control.

Susceptibility to seven antibiotics was determined using a standardized disk diffusion method according to Clinical and Laboratory Standards Institute guidelines.

Statistical analysis was performed with a Simpson's diversity index was calculated using the formula: $D=1-\Sigma[n*(n-1)/N*(N-1)]$, where n is the number of *E. coli* isolates in a particular clonotype, and N is the total number of isolates. Comparisons of proportions were tested using a two-tailed Fisher's exact test. Bacterial loads detected in urine by the 7-SNP typing test vs culture were compared using the two-sided paired t-test.

Example 5

This example shows the results of a computer-based analysis of high-resolution of *E. coli* clonotypes using the fumC and fimH nucleotide sequences of 2,556 isolates from eight clinical microbiology labs in the US, Germany, Poland and Russia. According to the analysis, the 2,559 isolates were divided among 54 unique binary septatypes (FIG. 1A). Six 'major' septatypes included more than 5% of isolates and comprised 47% of all isolates. Twenty three 'intermediate' septatypes each included 0.5-5% of isolates and together comprised 50% of the isolates. The remaining 25 septatypes were 'minor' with each including <0.5% of isolates. The overall diversity of major and intermediate septatypes was similar to that of MLST (FIG. 1B), which identified 6 major and 19 intermediate STs of the same size as defined by 7-SNP typing. Although there were nearly three times as many STs as septatypes (175 vs. 54), this difference was due entirely to the greater number of minor STs (150 in total) that together comprised only 13% of the isolates. This is reflected in comparable Simpson's diversity index values for 7-SNP typing and MLST (0.949 and 0.934, respectively).

Overall, in 27 septatypes (4 major, 10 intermediate, 15 minor) more than 90% of the isolates (97.2% on average) belonged to a single MLST-based clonal group. Such clonally homogeneous septatypes accounted for 54.1% of all isolates. A total of 17 STs could be predicted by the homogeneous septatypes, including multidrug-resistant ST131, ST69, ST38 and relatively susceptible ST95, ST73, ST14, ST12, ST569, and ST117. Moreover, several major STs like ST131, ST95, and ST73, were split by 7-SNP typing into smaller sub-ST clonal groups. For example, ST131 was split into fimH-based H30, H41, and H22 subclones (12), ST95 into its H41, H15, and H30 subclones, and ST73 into its H9, H10, and H30 subclones (13).

The remaining 27 septatypes were clonally heterogeneous, i.e., <90% of each septatype was of the same ST. Such major STs as drug-resistant ST58, ST88, ST354, ST648 and susceptible ST127, ST141, ST10, ST1876 were either split among different septatypes or could not be identified with the high probability.

Thus, binary combinations of seven disclosed SNPs selected from two highly variable genes, fimH and fumC, can genotype *E. coli* isolates with high resolution by splitting them into a large number of clonotypes. In most isolates, 7-SNP typing predicted the ST and, often, the sub-ST of origin with high accuracy. Accordingly, the disclosed clonotyping test described herein is a useful tool for both epidemiological analysis and clinical diagnostics.

Example 6

This example provides results providing using the disclosed clonotyping tests for determining antibiotic resistance and susceptibility. 7-SNP clonotyping sorted isolates into groups with distinctive antibacterial susceptibility profiles. In the total *E. coli* study population, the prevalence of resistance to six antibiotics most commonly used for empirical treatment UTI was as follows: amoxicillin/clavulanate and trimethoprim/sulfamethoxazole, 28% each; cefazolin, 23%; ciprofloxacin, 21%; nitrofurantoin, 11%; and ceftriaxone, 9%.

For each major and intermediate septatype, the prevalence of resistance to at least one antibiotic was significantly lower ('susceptible' septatype) or higher ('resistance' septatype) than in the total population (FIG. 2). Several prominent multi-drug resistant STs were split by 7-SNP typing into smaller clonal groups that had more distinct antimicrobial resistance profiles than both the average and the corresponding ST (Table 6). For example, the most dominant multi-drug resistant clonal group in *E. coli*, ST131, was split into 3 septatypes. Septatype 561 (corresponding to ST131-H-30 subclone) was highly resistant to ciprofloxacin (90.6%), while septatype 560 (ST131-H41) and 510 (ST131-H22) were almost entirely sensitive. At the same time, both 561 and 560, but to a much lesser extent 510, were highly resistant to trimethoprim/sulfamethoxazole. In ST69 (aka clonal group A) that is notorious for its resistance to trimethoprim/sulfamethoxazole, 7-SNP test identified septatype 351 that is almost entirely resistant to ciprofloxacin and 261 that is highly susceptible to most antibiotics, including trimethoprim/sulfamethoxazole. Similar splits that were informative from a resistance perspective were obtained by the 7-SNP test applied to ST58.

Overall, relative to the species average, the proportion of either resistant or susceptible septatypes was the largest for ciprofloxacin, for which 92% of isolates belonged to either resistant (34%) or susceptible (59%) septatypes (FIG. 3), with the average resistance prevalence in the former group being 51% and in the latter one only 4.4%. For other antibiotics, differences in the proportion of resistant and susceptible isolates were not as pronounced, but for all antibiotics except nitrofurantoin, most of the isolates were in septatypes with a resistance profile distinct from the average. Also, for all antibiotics except amoxicillin/clavulanate, the average resistance in the susceptible septatypes was below 10%.

Overall, 7-SNP typing performed well in splitting *E. coli* clinical isolates into clonotypes with distinctive antibacterial resistance profiles.

Figure 5:
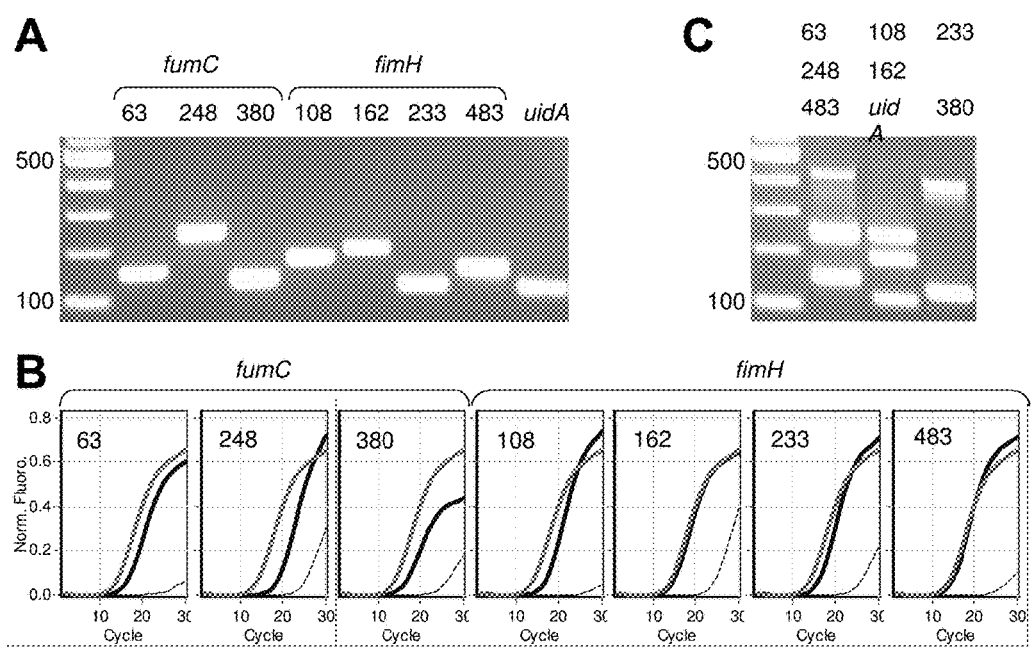
FIG. 5 shows examples of singleplex and multiplex PCR and qPCR profiles for the 7SNP test. (A) Seven singleplex PCR reactions detecting presence of SNPs; the eighth reaction is the uidA positive control of E. coli chromosomal DNA. (B) Seven qPCR profiles combining the uidA positive control (grey) with SNP-positive (thick black) and SNP-negative (thin black) reactions. (C) Two triplex and one duplex SNP-positive and uidA-positive PCR reactions. In panels (A) and (C) PCR products are loaded on 2% agarose gel, with left lane containing 100 bp DNA ladder. A random E. coli isolate with the 771 septatype from the reference collection was chosen to demonstrate the presence of all seven SNPs; the absence of individual SNPs in qPCR panel (B) was demonstrated using similarly random reference E. coli isolates with septatypes 510 (for SNPs 248, 108, 233 and 483) and 251 (for SNPs 63, 380 and 162).

7 pairs of SNP-specific primers and a pair of uidA-specific primers (for detection of *E. coli*) (Table 7) that, in conventional or quantitative PCR, yielded the predicted band sizes (FIGS. 5A and 5C) or signal (FIG. 5B), respectively, against the target DNA. We evaluated the ability of the SNP primers to recognize the corresponding SNPs in the background of 582 isolates with 60 fumC alleles and 156 fimH alleles that encompassed all naturally-occurring combinations of base pairs that are variable within the primer-annealing regions (see Example 4).

In only a few of the variable fumC or fimH alleles, the presence/absence of the targeted SNP could not be identified correctly by PCR, and these error-causing alleles were very rare in the reference set of 2,559 isolates. The total rate of erroneous 7 SNP typing test due to at least one of the 7 SNPs not detected correctly was projected to be only 2.1%.

To confirm the specificity of designed primers towards E. coli, we additionally tested them on isolates of various Enterobacteriaceae species: Klebsiella pneumoniae (10 isolates), Klebsiella oxytoca (4), Citrobacter freundii (5) and Citrobacter koserii (2), Enterobacter aerogenes (12), Proteus mirabilis (6), Pseudomonas aeruginosa (3), Serratia marsenscens (3) and Morhanella morganii (5). Both the SNP-specific reactions and the uidA control produced negative results in all non-E. coli isolates with the exception of one isolate designated by 16S typing as E. aerogenes.

Thus, the newly designed SNP-specific primers demonstrated a robust ability to distinguish the targeted SNPs despite some background sequence variation in the primer-annealing regions.

Figure 4:
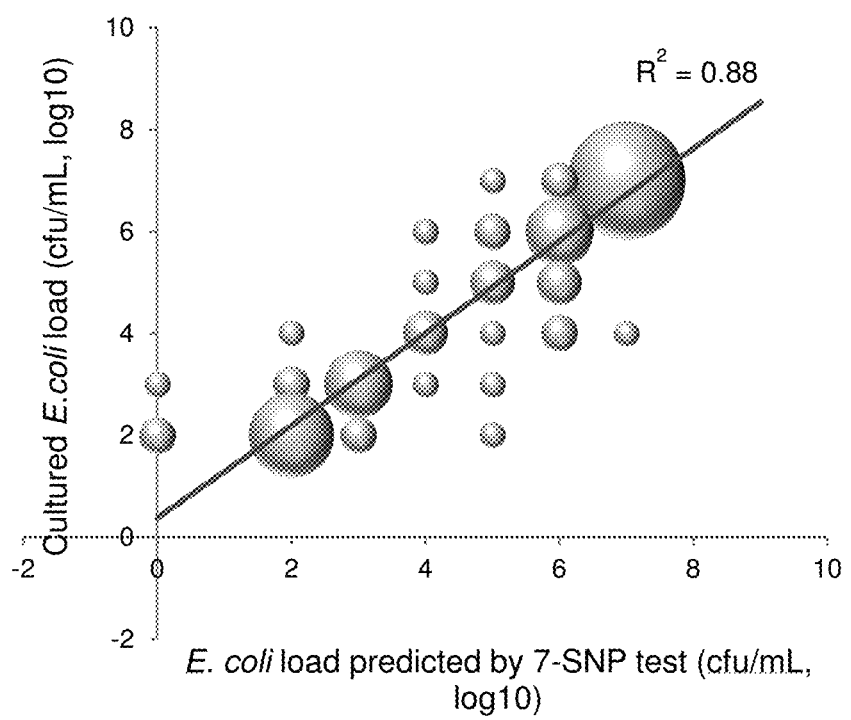
FIG. 4 shows detection of E. coli in urine by the disclosed 7-SNP clonotyping versus culturing. A total of 77 urine samples that had positive E. coli growth are plotted, with the E. coli load determined by the disclosed 7-SNP test in qPCR on the Y-axis and culture-derived E. coli load on the Y-axis. The size of bubbles was directly proportional to the number of urine samples with each combination of determined cfu/ml. The regression line represents the linear least square fit, with $\beta=0.97$, $R^2=0.88$ and P value <0.0001.

The disclosed 7-SNP typing test can identify E. coli clonotypes directly from urine specimens. In addition to the validation using pure bacterial cultures, the qPCR-based 7-SNP typing test was performed on bacterial DNA obtained from clinical urine samples—77 were positive and 83 negative for E. coli as determined by culture. In the E. coli culture-negative samples, the 7-SNP test was positive in 2 urines (98% specificity). In E. coli culture-positive urines, 74 were positive in the 7-SNP typing test, (96% sensitivity), and the identified clonotype matched that of the cultured isolate in all but one sample. Furthermore, the 7-SNP test was positive and detected the same clonotype as was isolated from culture in all 49 urine samples that had clinically significant levels of E. coli (at least $10^4$ cfu/ml). Overall, there was a strong correlation between the bacterial load determined by culture and that predicted by the qPCR test based on the E. coli-specific uidA probe (FIG. 4). In a lab is 11 three qPCR-negative but culture-positive urine samples, the bacterial load was low—$10^2$ cfu/ml (in two samples) or $10^3$ cfu/ml (in one sample). Overall, multi-E. coli specimen occurred in <1%.

Thus, the disclosed 7-SNP typing test can detect E. coli in urine samples and reliably identify the corresponding clonotype, performing essentially as well as the standard culture procedure quantitatively.

Example 7

This example provides the results of a clinical field trial showing the performance of the disclosed 7 SNP-based clonotyping test (CLT test) conducted at an HMO (health maintenance organization, Group Health Urgent Care). The disclosed test kit and process was conducted on urinalysis-positive urine samples on-site at the HMO urgent care clinical laboratory. All urine samples obtained at Urgent Care facility were tested by the 7-SNP-based CLT (clonotyping) test and by a standard E. coli culturing test. Out of total of 147 urine samples, 90 were positive in urinalysis test, according to the HMO facility. Out of those, 35 samples were positive for E. coli culture, and 34 of those were positive in CLT test (94%). Additionally, 2 samples were positive for the CLT test, but culture was negative for E. coli. Out of 57 urinalysis-negative samples only 1 was positive for E. coli culture and CLT test both, and 1 more sample was positive only for CLT test. In summary, a positive CLT test was an excellent predictor of positive E. coli growth (34/36 vs 3/111, P<0.0001), and positive urinalysis was excellent predictor of both positive E. coli growth (35/90 vs 1/57, P<0.0001) and positive CLT test (35/90 vs 2/57, P<0.0001). Table 8 summarizes the results achieved.

TABLE 8

|  |  | Total (N = 147) | Urinalysis Positive (N = 90) | Urinalysis Negative (N = 57) |
|---|---|---|---|---|
| Positive E. coli growth | Total[a] | 36 (24.5%) | 35 (39%) | 1 (1.8%) |
|  | Positive CLT[b] | 34 (94.4%) | 33 (94.3%) | 1 (100%) |
|  | Negative CLT[c] | 2 (5.6%) | 1 (3.0%) | 0 (0.0%) |
| Negative E. coli growth | Total[a] | 111 (75%) | 55 (61%) | 56 (98%) |
|  | Positive CLT[b] | 3 (2.7%) | 2 (3.6%) | 1 (1.8%) |
|  | Negative CLT[c] | 108 (97%) | 109 (98%) | 55 (98%) |

Figure 6:
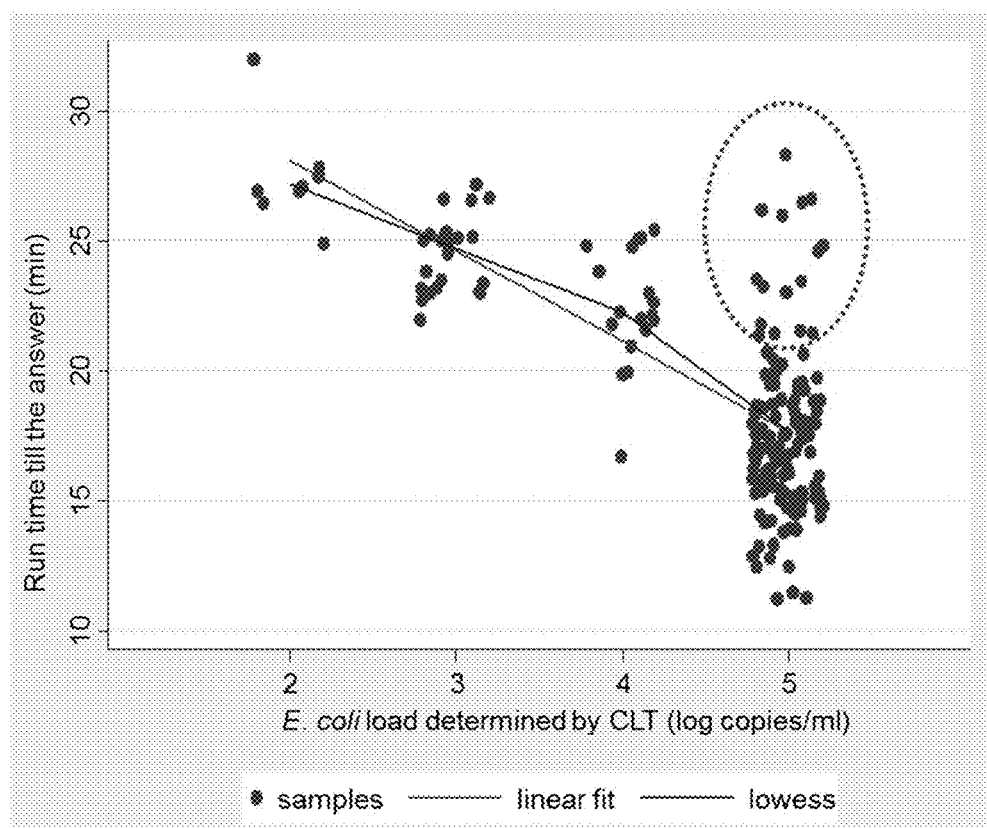
FIG. 6 shows the time it took for a positive result in each case against the actual load of E. coli in urine determined by the disclosed SNP-7 test kit and process (N=177 urine samples analyzed here). Using this test we detected as low as $10^2$ DNA copies/mL, whereas the standard culturing technique in the same HMO urgent care lab (and other clinical labs as well) detected only $10^3$ cfu/ml. A clinically significant level is considered to be $10^4$ cfu/ml and higher.

In the period from April until December 2015, two technicians worked at the urgent care clinical lab performing the CLT test on urine samples. They timed how long it took them to process each sample and to at which cycle (1 cycle=1 min) of the reaction they were able to tell if there was E. coli DNA in the sample, how much, and what septatype. The timing of the reaction was analyzed in Table 9 below FIG. 6. FIG. 6 shows the time it took for a positive result in each case against the actual load of E. coli in urine determined by the disclosed SNP-7 test kit and process (N=177 urine samples analyzed here). Using this test we detected as low as $10^2$ DNA copies/mL, whereas the standard culturing technique in the same HMO urgent care lab (and other clinical labs as well) detected only $10^3$ cfu/ml. A clinically significant level is considered to be $10^4$ cfu/ml and higher. FIG. 6 shows a majority of clinically significant samples were well below a 22 minute cutoff. When combined with an 8 min-long $1^{st}$ sample preparation step would constitute about 30 minutes to run the whole test.

There were few samples from the high-load group that required, surprisingly, longer time for a positive answer (circled in red on the Figure). Some of them were so-called "dirty" samples in that they contained additional substances that interfered with the PCR reaction, making the read-out difficult, thus requiring longer time to process.

TABLE 9

| CLT reaction time in Rotorgene ® Q to tell if: | Mean ± SD (min) | Min ÷ Max (min) | Percentiles: 25%, 50%, 75% (min) |
|---|---|---|---|
| A sample is E. coli-positive >$10^2$ copies DNA per 1 mL of urine (N = 177) | 19.3 ± 4.1 | 11 ÷ 32 | 16, 18, 23 |
| A sample is E. coli-positive >$10^4$ copies DNA per 1 mL of urine (N = 146) | 18.1 ± 3.3 | 11 ÷ 27 | 16, 18, 20 |

TABLE 9-continued

| CLT reaction time in Rotorgene ® Q to tell if: | Mean ± SD (min) | Min ÷ Max (min) | Percentiles: 25%, 50%, 75% (min) |
|---|---|---|---|
| Septatype for any *E. coli*-positive sample (N = 177) | 23.8 ± 3.9 | 16 ÷ 35 | 21, 23, 27 |
| Septatype for >10^4 *E. coli*-positive sample (N = 146) | 22.7 ± 3.3 | 16 ÷ 35 | 21, 22, 24 |

The procedure used was: Step 1: initial processing of urine sample using a Chelex procedure. Briefly, the urine sample was treated with Chelex beads to isolate DNA. This step on took 8 min on average. Step 2:® on Rotorgene Q instrument (60 seconds per cycle). qPCR, can vary in length depending on what is the load of bacteria in the initial sample (cfu/mL), which translates into the load of *E. coli* DNA in the Chelex-purified sample (copies/mL). The presence of *E. coli* can be detected as early as after 11 min (11+8=19 min for whole test), with average detection time 19.3±4.1 min (27.3 min for the whole test).

The determination of septatype of the present *E. coli* required an additional 3-5 min on average because the reliability of the result depended on how advanced the reaction curves were. Time to tell positive results also varied depending on the "dirtiness" of the urine specimen. "Dirtiness" of the sample includes presence of cell debris, high protein, mucus etc., as well as chromogenic substances that can interfere with either PCR reaction or fluorescent readout.

Figure 7:
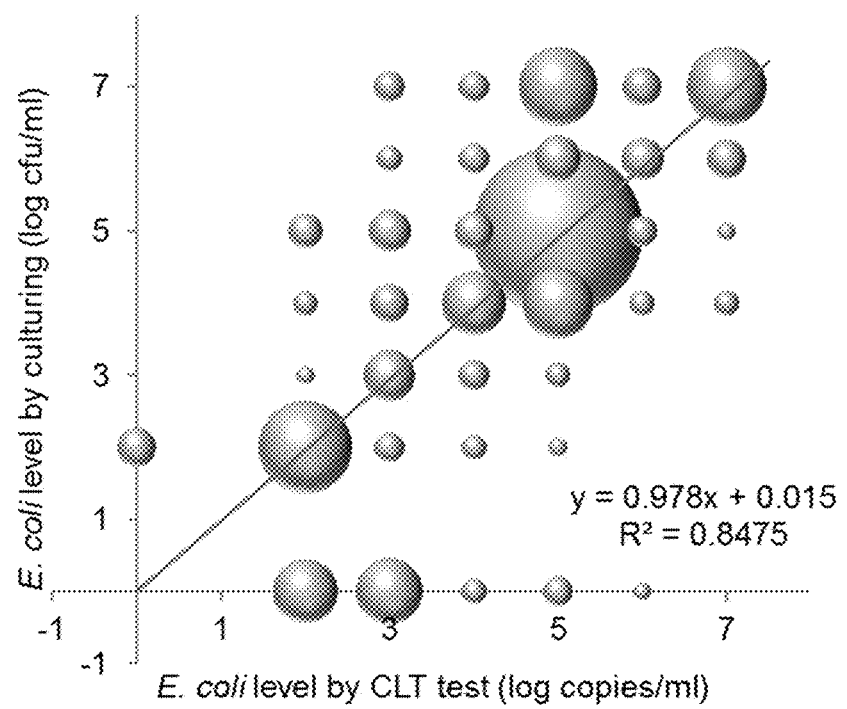
FIG. 7 shows 327 samples positive for either CLT test or culturing or both. The size of the bubble represents the number of samples in each group. The straight line represents the fitted values for a simple linear regression on all samples with valid data (N=736). Red lines show the cutoff for clinically-significant levels of bacterial load. Grey line represents the least square fit for simple linear regression. From this fit we estimate that for every 1 log increase detected by the SNP-7 test the culturing will detect on average 0.97 log increase (95% confidence intervals from 0.92 to 1 log, P<0.0001, Pearson's correlation coefficient $R^2=0.85$).

There was a correlation detected between *E. coli* levels detected between standard culture tests (taking 2-3 days) and the disclosed SNP-7 test. 327 samples positive for either CLT test or culturing or both are plotted in FIG. 7. The size of the bubble represents the number of samples in each group. The straight line represents the fitted values for a simple linear regression on all samples with valid data (N=736). Red lines show the cutoff for clinically-significant levels of bacterial load.

In total, 750 urinalysis-positive samples from the HMO urgent care lab were processed in CLT test and standard culturing test. Out of those, 409 were negative for *E. coli* presence both in CLT test and in culture. 14 more samples were excluded from further analysis due to no data logged on the *E. coli* load. The rest, 327 culture- and CLT-test-positive samples, are plotted in FIG. 7. These 327 samples exhibited strong correlation between the *E. coli* levels determined in CLT test and in culturing. From the simple linear regression we estimate that with each 10-times ($\log_{10}=1$) increase in the CLT-determined level of *E. coli* the increase in *E. coli* growth will be on average 9.8 times (CI 95% from 9.5 to 10.0, P<0.0001). This means that there is an extremely good correlation between the *E. coli* levels in urine detected by both methods. Overall, when comparing the results of CLT test to the standard culture test, the sensitivity of the CLT test was 98.4% for all detection level and 100% for detection of *E. coli* in urine at the level considered clinically significant ($10^4$ cfu/ml and above).

The *E. coli* septatypes identified in the field study (out of 750 samples, see above) were compared to a reference collection of *E. coli* to (1) compare the clonotypes distribution, (2) compare the overall resistance profile, and (3) use the reference collection to predict if antibiotics can or cannot be allowed for use in each case in the field study (as a Lookup Table). Further, the prediction from (3) was compared to actual resistance of individual isolates and to clinical data regarding the prescription of antibiotics in each case. From this we can see if the implementation of the CLT test would improve the choice of antibacterial therapy.

A reference collection of *E. coli* included 1227 isolates that were from the same HMO (only from Group Health), only from urine samples, unique (mostly one isolate per patient; 10 patients had mixed *E. coli* cultures with different septatypes and antibiotic resistance profiles), and isolated in the period from 2010-2013. Both septatypes and antimicrobial profiles were identified.

The antibiotic profiles of major septatypes from the reference *E. coli* collection (Lookup Table) is provided in Table 10 (FIG. 11).

In total, 1227 *E. coli* isolated from the HMO (Group Health) clinical lab in 2010-2013 were analyzed. All had their clonotype type determined and resistance to antibiotics tested. Septatypes were deduced from CH types (clonotypes). The average resistance across isolates within each septatypes is given in Table 10. Red indicates resistance >30%. Yellow: more than 15% but less than 30%. Green: less than 15%.

Out of 750 samples, 308 isolates from 306 samples had unique clonotypes (2 patients had mixed culture in urine). Out of 308 isolates, 303 (98.4%) belonged to septatypes that had been described previously for the reference set of *E. coli*. Altogether, 308 isolates were distributed into 36 septatypes, of which 32 were previously described, and 4 were newly identified.

More than 98% of *E. coli*—positive urine samples were infected with bacteria of a previously described septatype, which allows for clone-based prediction of antibacterial resistance based on a reference Lookup Table. In case of a new (unknown) septatype, the species-specific (was overall for *E. coli*) resistance is used for prediction of an antibiotic.

When comparing antibiotic resistance in *E. coli* isolates from this Field Trial with the Reference Lookup-Table resistance, Table 11 (FIG. 12) shows the overall resistance levels were comparable for all antibiotics, although there was a significant increase in resistance to Fluorqinolones (P<0.05). For clone-based prediction of bacterial resistance of field study isolates we used a 15% resistance as a cutoff for rejection of an antibiotic.

For antibiotic prescriptions, Table 12 (FIG. 13) shows a total of 750 cases were analyzed; 291 patients had *E. coli* identified in urine by CLT test, confirmed by culture results. Overall, 82% of patients positive for *E. coli* in urine (236/291) were prescribed antibiotics at the day of the visit. The most often prescribed group of antibiotics were fluorquinolones (51.7%), followed by Bactrim (28.4%).

For drug-bug mismatches, out of 236 cases where *E. coli* in urine was determined by CLT test and culturing, and an antibiotic was prescribed around the index visit day, in 41 (17.4%) cases, the *E. coli* isolate was resistant to the prescribed antibiotic. This is called a drug-bug mismatch. The rate of drug-bug mismatches did not differ significantly from the overall resistance rate to this antibiotics, confirming that the choice of the therapy was indeed most likely empirical. This is shown in Table 13 (FIG. 14).

For further analysis we included all 291 cases when *E. coli* was identified both by CLT test and by culture, including 236 cases where antibiotic was prescribed at the visit day, and the rest 55 cases. Based on the identified clonotype we assigned to each case a value for each antibiotic—if the resistance in this clonotype to this antibiotic was less than 15%, it was allowed for use; otherwise it was rejected. From the Table 14 (FIG. 15), only ampicillin group of antibiotics was almost always rejected, based on the clonotype resistance (1.7% allowed cases). For the rest of antibiotics, they were allowed in 34.7% cases for Bactrim (aka, Trim-Sulfa®), 75.6% cases for fluorquionolones.

For drug-bug mismatch in antibiotics prescribed based on CLT test, in each case for each allowed antibiotic, we checked if the actual *E. coli* isolate was sensitive to this antibiotic. Then, for each antibiotic we counted the number of resistant isolates as percentage from total allowed isolates—deducing the drug-bug mismatch rate after the CLT test. For all antibiotics the drug-bug mismatch rate was significantly reduced by using the CLT test results for prediction, with the overall rate reduction from 17.4% to 4.3%—more than 4 times. This is shown in Table 15 (FIG. 16).

Accordingly, the CLT test was highly efficient in identification of cultivable *E. coli* in urine samples, especially at clinically significant levels. The CLT test can be performed at the point-of-care facility within the time limits of a patient's visit (less than 1 hour). The CLT test allowed for efficient prediction of which antibiotic can be used for treatment, thus reducing the chance of a drug-bug mismatch more than 4 fold over guessing.

I claim:

1. A method for determining antibiotic susceptibility of *E. coli*, comprising
   (a) amplifying polynucleotide fragments from an *E. coli* genome using forward and reverse primer pairs specific for at least seven different *E. coli* single nucleotide polymorphisms (SNPs), wherein the SNPs comprise fumC-63, fumC-248, fumC-380, fimH-162, fimH-233, fimH-483, and fimH-108, and wherein the primer pairs comprise one or more of the following primer pairs:
   (i) a fum-63 forward primer comprising the nucleic acid sequence of SEQ ID NO:5 and a fum-63 reverse primer comprising the nucleic acid sequence of SEQ ID NO:6 or SEQ ID NO:8,
   (ii) a fumC-248 forward primer comprising the nucleic acid sequence of SEQ ID NO:7 and a fumC-248 reverse primer comprising the nucleic acid sequence of SEQ ID NO:8,
   (iii) a fumC-380 forward primer comprising the nucleic acid sequence of SEQ ID NO:9, 11, or 12 and a fumC-380 reverse primer comprising the nucleic acid sequence of SEQ ID NO: 10,
   (iv) a fimH-108 forward primer comprising the nucleic acid sequence of SEQ ID NO: 13 and a fimH-108 reverse primer comprising the nucleic acid sequence of SEQ ID NO: 14,
   (v) a fimH-162 forward primer comprising the nucleic acid sequence of SEQ ID NO:15 and a fimH-162 reverse primer comprising the nucleic acid sequence of SEQ ID NO:16,
   (vi) a fimH-233 forward primer comprising the nucleic acid sequence of SEQ ID NO: 17 and a fimH-233 reverse primer comprising the nucleic acid sequence of SEQ ID NO: 18 or SEQ ID NO: 20, and
   (vii) a fimH-483 forward primer comprising the nucleic acid sequence of SEQ ID NO: 19 and a fimH-483 reverse primer comprising the nucleic acid sequence of SEQ ID NO:20;
   (b) detecting the presence or absence of one or more of the at least seven SNPs in the *E. coli* genome to identify the *E. coli* clonotype; and
   (c) comparing the *E. coli* clonotype to a Lookup Table to determine the *E. coli*'s susceptibility to one or more antibiotics.

2. The method of claim 1, wherein the Lookup Table is Lookup Table 1.

3. A kit comprising
   (a) forward primer and reverse primer pairs for at least seven *E. coli* single nucleotide polymorphisms (SNPs), wherein the SNPs comprise fumC-63, fumC-248, fumC-380, fimH-162, fimH-233, fimH-483, and fimH-108, and wherein the primer pairs comprise one or more of the following primer pairs:
   (i) a fumC-248 forward primer comprising the nucleic acid sequence of SEQ ID NO:7 and a fumC-248 reverse primer comprising the nucleic acid sequence of SEQ ID NO:8,
   (ii) a fimH-108 forward primer comprising the nucleic acid sequence of SEQ ID NO:13 and a fimH-108 reverse primer comprising the nucleic acid sequence of SEQ ID NO:14,
   (iii) a fimH-233 forward primer comprising the nucleic acid sequence of SEQ ID NO: 17 and a fimH-233 reverse primer comprising the nucleic acid sequence of SEQ ID NO: 18 or SEQ ID NO:20, and
   (iv) a fimH-483 forward primer comprising the nucleic acid sequence of SEQ ID NO: 19 and a fimH-483 reverse primer comprising the nucleic acid sequence of SEQ ID NQ:20;
   (b) a Lookup Table; and
   (c) an instruction for identifying an *E. coli* clonotype and determining the *E. coli*'s susceptibility to one or more antibiotics.

4. The kit claim 3, wherein the Lookup Table is Lookup Table 1.

5. The kit of claim 3, wherein at least two of the primer pairs selected from (a)(i)-(a)(iv) are mixed in a single container.

6. A method for treating an *E. coli* infection in a patient, the method comprising administering to a patient in need thereof an effective amount of one or more antibiotics, wherein the *E. coli* infecting the patient is known to be susceptible to the one or more administered antibiotics as determined by the method of claim 1.

7. The method of claim 6, wherein the one or more antibiotics are selected from trimethoprim-sulfamethoxazole, cefazolin, ciproflaxin, nitrofurantoin, ceftriaxone, amoxicillin-clavulanate, or any combination thereof.

8. The method of claim 1, wherein the *E. coli* is from a patient sample selected from the group consisting of urine, blood, saliva, tears, and a skin swipe.

9. The method of claim 8, wherein the sample comprises urine from a patient suspected of having a urinary tract infection.

10. The method of claim 9, wherein the urine sample was fractionated to separate the bacterial components from non-bacterial nucleic acids, ureas, and solids.

11. The method of claim 10, wherein the fractionated bacteria were lysed prior to performing the amplifying step.

12. The method of claim 1, wherein the primer pairs comprise:
   (i) a fum-63 forward primer comprising the nucleic acid sequence of SEQ ID NO:5 and a fum-63 reverse primer comprising the nucleic acid sequence of SEQ ID NO:6 or SEQ ID NO:8;
   (ii) a fumC-248 forward primer comprising the nucleic acid sequence of SEQ ID NO:7 and a fumC-248 reverse primer comprising the nucleic acid sequence of SEQ ID NO:8;
   (iii) a fumC-380 forward primer comprising the nucleic acid sequence of SEQ ID NO:9, 11, or 12 and a fumC-380 reverse primer comprising the nucleic acid sequence of SEQ ID NO:10;
   (iv) a fimH-108 forward primer comprising the nucleic acid sequence of SEQ ID NO: 13 and a fimH-108 reverse primer comprising the nucleic acid sequence of SEQ ID NO: 14;
   (v) a fimH-162 forward primer comprising the nucleic acid sequence of SEQ ID NO:15 and a fimH-162 reverse primer comprising the nucleic acid sequence of SEQ ID NO:16;
   (vi) a fimH-233 forward primer comprising the nucleic acid sequence of SEQ ID NO: 17 and a fimH-233 reverse primer comprising the nucleic acid sequence of SEQ ID NO: 18 or SEQ ID NO: 20; and
   (vii) a fimH-483 forward primer comprising the nucleic acid sequence of SEQ ID NO: 19 and a fimH-483 reverse primer comprising the nucleic acid sequence of SEQ ID NO:20.

13. The method of claim 1, wherein identifying the *E. coli* clonotype further comprises performing a multiplex nucleic acid amplification process reaction with SNP-specific B primers for a SNP within a gene locus selected from fumC, fimH, adk, gryB, icd, mdh, purA, recA, or a combination thereof, provided that the SNP within fumC or fimH is not fum-63, fumC-248, fumC-380, fimH-162, fimH-233, fimH-483, or fimH-108.

14. The method of claim 13, wherein the fimH-specific primers comprise a forward primer comprising the nucleotide sequence shown in SEQ ID NO:1 and a reverse primer comprising the nucleotide sequence shown in SEQ ID NO:2.

15. A method for determining the presence or absence of a single nucleotide polymorphism (SNP) in an *E. coli*, the method comprising performing a nucleic acid amplification process on DNA isolated from *E. coli* obtained from a patient sample, wherein the nucleic acid amplification process comprises use of forward and reverse primer pairs specific for fumC-63, fumC-248, fumC-380, fimH-162, fimH-233, fimH-483, and fimH-108, and determining the presence or absence of one or more of the fumC-63, fumC-248, fumC-380, fimH-162, fimH-233, fimH-483, and fimH-108 SNPs.

16. The method of claim 15, wherein:
  (a) the forward primer for fum-63 comprises the nucleic acid sequence shown in SEQ ID NO:5 and the reverse primer for fum-63 comprises the nucleic acid sequence shown in SEQ ID NO:6 or SEQ ID NO:8;
  (b) the forward primer for fumC-248 comprises the nucleic acid sequence shown in SEQ ID NO:7 and the reverse primer for fumC-248 comprises the nucleic acid sequence shown in SEQ ID NO:8;
  (c) the forward primer for fumC-380 comprises the nucleic acid sequence shown in any one of SEQ ID NOS:9, 11, or 12, and the reverse primer for fumC-380 comprises the nucleic acid sequence shown in SEQ ID NO: 10;
  (d) the forward primer for fimH-108 comprises the nucleic acid sequence shown in any one of SEQ ID NO: 13, and the reverse primer for fimH-108 comprises the nucleic acid sequence shown in SEQ ID NO: 14;
  (e) the forward primer for fimH-162 comprises the nucleic acid sequence shown in SEQ ID NO: 15 and 16 and the reverse primer for fimH-162 comprises the nucleic acid sequence shown in SEQ ID NO:16;
  (f) the forward primer for fimH-233 comprises the nucleic acid sequence shown in SEQ ID NO: 17, and the reverse primer for fimH-233 comprises the nucleic acid sequence shown in SEQ ID NO:18 or SEQ ID NO:20; and/or
  (g) the forward primer for fimH-483 comprises the nucleic acid sequence shown in SEQ ID NO: 19 and the reverse primer for fimH-483 comprises the nucleic acid sequence shown in SEQ ID NO:20.

17. The method of claim 15, wherein the sample is selected from the group consisting of urine, blood, saliva, tears, and a skin swipe.

18. The method of claim 17, wherein the sample comprises urine from a patient suspected of having a urinary tract infection.

19. The kit of claim 3, wherein the primer pairs further comprise one or more of the following primer pairs:
  (i) a fum-63 forward primer comprising the nucleic acid sequence of SEQ ID NO:5 and a fum-63 reverse primer comprising the nucleic acid sequence of SEQ ID NO:6 or SEQ ID NO:8,
  (ii) a fumC-380 forward primer comprising the nucleic acid sequence of SEQ ID NO:9, 11, or 12 and a fumC-380 reverse primer comprising the nucleic acid sequence of SEQ ID NO:10, and
  (iii) a fimH-162 forward primer comprising the nucleic acid sequence of SEQ ID NO:15 and a fimH-162 reverse primer comprising the nucleic acid sequence of SEQ ID NO:16.

20. The kit of claim 19, wherein the primer pairs comprise:
  (i) a fum-63 forward primer comprising the nucleic acid sequence of SEQ ID NO:5 and a fum-63 reverse primer comprising the nucleic acid sequence of SEQ ID NO:6 or SEQ ID NO:8;
  (ii) a fumC-248 forward primer comprising the nucleic acid sequence of SEQ ID NO:7 and a fumC-248 reverse primer comprising the nucleic acid sequence of SEQ ID NO:8;
  (iii) a fumC-380 forward primer comprising the nucleic acid sequence of SEQ ID NO:9, 11, or 12 and a fumC-380 reverse primer comprising the nucleic acid sequence of SEQ ID NO:10;
  (iv) a fimH-108 forward primer comprising the nucleic acid sequence of SEQ ID NO:13 and a fimH-108 reverse primer comprising the nucleic acid sequence of SEQ ID NO:14;
  (v) a fimH-162 forward primer comprising the nucleic acid sequence of SEQ ID NO:15 and a fimH-162 reverse primer comprising the nucleic acid sequence of SEQ ID NO:16;
  (vi) a fimH-233 forward primer comprising the nucleic acid sequence of SEQ ID NO: 17 and a fimH-233 reverse primer comprising the nucleic acid sequence of SEQ ID NO:18 or SEQ ID NO:20; and
  (iv) a fimH-483 forward primer comprising the nucleic acid sequence of SEQ ID NO: 19 and a fimH-483 reverse primer comprising the nucleic acid sequence of SEQ ID NQ:20.

* * * * *